US011360065B2

(12) United States Patent
Lynch et al.

(10) Patent No.: US 11,360,065 B2
(45) Date of Patent: Jun. 14, 2022

(54) CALIBRATION SYSTEMS AND METHODS FOR ANALYTE DETECTORS

(71) Applicant: TELEDYNE FLIR DETECTION, INC., Stillwater, OK (US)

(72) Inventors: John B. Lynch, Stillwater, OK (US); Martin Sanders, Morrison, OK (US); Chris Willis, Stillwater, OK (US)

(73) Assignee: Teledyne FLIR Detection, Inc., Stillwater, OK (US)

(*) Notice: Subject to any disclaimer, the term of this patent is extended or adjusted under 35 U.S.C. 154(b) by 526 days.

(21) Appl. No.: 16/352,661

(22) Filed: Mar. 13, 2019

(65) Prior Publication Data

US 2019/0285595 A1 Sep. 19, 2019

Related U.S. Application Data

(60) Provisional application No. 62/644,302, filed on Mar. 16, 2018.

(51) Int. Cl.
*G01N 33/00* (2006.01)
*G01N 33/94* (2006.01)

(52) U.S. Cl.
CPC ..... *G01N 33/0006* (2013.01); *G01N 33/0057* (2013.01); *G01N 33/94* (2013.01)

(58) Field of Classification Search
CPC . G01N 33/0006; G01N 33/94; G01N 33/0057
USPC ......................................................... 436/43
See application file for complete search history.

(56) References Cited

U.S. PATENT DOCUMENTS

| 3,884,640 A | * | 5/1975 | Lock ................. G01N 33/492 422/82.03 |
| 4,473,458 A | * | 9/1984 | Schwartz ............ G01N 27/283 204/416 |
| 4,478,222 A | * | 10/1984 | Koning .............. A61B 5/14542 600/348 |
| 4,654,127 A | * | 3/1987 | Baker .................. B01L 3/5023 204/401 |
| 4,786,394 A | * | 11/1988 | Enzer ................ G01N 33/4925 128/DIG. 3 |
| 4,863,016 A | * | 9/1989 | Fong ................... A61M 25/002 206/210 |
| 4,871,439 A | * | 10/1989 | Enzer .................. G01N 33/492 204/401 |
| 4,935,106 A | * | 6/1990 | Liston ............... G01N 27/3271 204/400 |
| 4,940,527 A | * | 7/1990 | Kazlauskas ......... G01N 33/491 204/401 |

(Continued)

*Primary Examiner* — Arlen Soderquist
(74) *Attorney, Agent, or Firm* — Haynes and Boone, LLP

(57) ABSTRACT

Techniques are disclosed for calibration systems and methods for analyte detectors. In one example, a system may include a calibration device configured to operate with an analyte detector. The calibration device may include a chamber configured to receive a sample and pass at least a portion of the sample including analytes to the analyte detector for examination. The calibration device may further include a reservoir including a calibrant and configured to be selectively positioned in the chamber as the sample to provide the portion of the sample including the analytes to calibrate the analyte detector. Additional systems and related methods are provided.

18 Claims, 14 Drawing Sheets

(56) References Cited

U.S. PATENT DOCUMENTS

| | | | |
|---|---|---|---|
| 5,004,583 A * | 4/1991 | Guruswamy | G01N 27/4165 204/401 |
| 5,064,618 A * | 11/1991 | Baker | G01N 33/48707 422/82.01 |
| 5,080,865 A * | 1/1992 | Leiner | G01N 1/28 204/401 |
| 5,092,217 A | 3/1992 | Achter et al. | |
| 5,096,669 A * | 3/1992 | Lauks | B01L 3/502707 204/403.02 |
| 5,230,863 A * | 7/1993 | Salpeter | G01N 21/274 250/252.1 |
| 5,232,668 A * | 8/1993 | Grant | G01N 21/474 422/429 |
| 5,243,982 A * | 9/1993 | Mostl | A61B 5/14532 128/DIG. 12 |
| 5,325,853 A * | 7/1994 | Morris | G01N 27/4165 204/403.02 |
| 5,452,600 A | 9/1995 | Davies et al. | |
| 5,493,890 A | 2/1996 | Dussault et al. | |
| 5,511,880 A * | 4/1996 | Macemon | B01F 9/002 366/213 |
| 5,747,666 A * | 5/1998 | Willis | G01N 27/3274 204/194 |
| 5,789,258 A | 8/1998 | Drinkwine et al. | |
| 6,306,347 B1 * | 10/2001 | Mason | G01N 21/8483 422/417 |
| 6,451,606 B1 * | 9/2002 | Konig | G01N 33/4875 204/409 |
| 7,448,248 B2 | 11/2008 | Carey et al. | |
| 7,709,788 B2 | 5/2010 | Geraghty et al. | |
| 7,757,539 B2 | 7/2010 | Szabo et al. | |
| 8,038,946 B1 | 10/2011 | Harper et al. | |
| 8,932,537 B2 | 1/2015 | Haas et al. | |
| 9,005,524 B2 | 4/2015 | Deans et al. | |
| 9,448,180 B2 * | 9/2016 | O'Dell | G01N 33/0057 |
| 10,458,919 B2 * | 10/2019 | O'Dell | G01N 21/783 |
| 2003/0143746 A1 * | 7/2003 | Sage, Jr. | A61B 5/14865 436/8 |
| 2003/0224523 A1 * | 12/2003 | Thornberg | B01L 3/502738 436/43 |
| 2004/0163970 A1 * | 8/2004 | Sin | G01N 33/4915 205/792 |
| 2005/0010135 A1 * | 1/2005 | Fischer | B01L 3/502 600/573 |
| 2006/0013744 A1 * | 1/2006 | Mikkelsen | B32B 27/32 422/400 |
| 2006/0088442 A1 | 4/2006 | Eckels et al. | |
| 2006/0200070 A1 * | 9/2006 | Callicoat | A61B 5/150213 604/66 |
| 2008/0067336 A1 * | 3/2008 | Goodley | H01J 49/168 250/252.1 |
| 2008/0098794 A1 * | 5/2008 | Perry | H01J 49/00 73/1.06 |
| 2008/0312518 A1 * | 12/2008 | Jina | A61B 5/1495 600/345 |
| 2009/0133469 A1 | 5/2009 | Atkinson et al. | |
| 2009/0205398 A1 * | 8/2009 | Nagel | G01N 27/622 73/1.02 |
| 2011/0146381 A1 * | 6/2011 | Wells | G01N 30/7206 73/23.41 |
| 2012/0197544 A1 * | 8/2012 | Briscoe | G01N 1/2273 702/25 |
| 2012/0304729 A1 * | 12/2012 | O'Dell | G01N 21/783 73/1.02 |
| 2013/0142709 A1 * | 6/2013 | Lin | G01N 27/26 422/538 |
| 2014/0371553 A1 * | 12/2014 | Winkelman | A61B 5/14503 600/316 |
| 2015/0323511 A1 * | 11/2015 | Hendry | A61B 5/1495 73/1.06 |
| 2016/0033410 A1 * | 2/2016 | Ja | G01N 33/227 436/171 |
| 2017/0092152 A1 * | 3/2017 | Wichert | G09B 5/02 |
| 2018/0003689 A1 | 1/2018 | Shelton et al. | |
| 2018/0180599 A1 | 6/2018 | Wald et al. | |
| 2018/0292380 A1 * | 10/2018 | Kurkowski | G01N 33/48771 |

* cited by examiner

CALIBRATION SYSTEMS AND METHODS FOR ANALYTE DETECTORS

CROSS REFERENCE TO RELATED APPLICATIONS

This application claims the benefit of and priority to U.S. Provisional Patent Application No. 62/644,302 filed Mar. 16, 2018 and entitled "CALIBRATION SYSTEMS AND METHODS FOR ANALYTE DETECTORS," which is incorporated herein by reference in its entirety.

TECHNICAL FIELD

The present disclosure relates to analyte detectors and, more particularly, to calibration systems and methods for analyte detectors.

BACKGROUND

Detection of explosives, narcotics, and other materials of interest is an area of ongoing global concern for security and other purposes. Conventional detection systems, such as X-ray diffraction, nuclear quadruple resonance, ion mobility spectrometry, mass spectrometry, and gas chromatography are known and are highly sensitive and effective. Such systems, however, are often expensive, difficult to maintain, and may not be easily implemented in more convenient portable form factors.

Unfortunately, many portable detection devices may still encounter difficulties in the field. As such devices are used, it may become necessary to calibrate their analyte detectors to ensure accurate readings are provided and to prevent false positive or false negative readings.

For example, if an analyte detector receives a particularly large amount of analytes, its associated analyte reporter may become temporarily saturated which may affect future readings. Alternatively, if the analyte reporter becomes depleted, it may be difficult for a user to discern whether a negative reading is indeed true, or simply the result of a non-responsive analyte reporter. Accordingly, in general, such devices cannot rely solely on preset factory calibrations to maintain accuracy.

Conventional techniques for calibrating such devices often involve manually introducing materials to the system having a predetermined response by an analyte reporter, examining the materials in a conventional manner, and reviewing the results. Only after this extensive effort will the user be able to discern whether a particular analyte reporter is operating as expected. This is generally inconvenient and may require the user to maintain separate supplies of materials and related equipment for performing such calibration operations.

Moreover, such manual approaches may be subject to human error, as they require the user to provide the correct test materials, and in the correct quantities, in order to obtain a reliable calibration result. Therefore, there is a need to provide improved ways to facilitate analyte detection for materials of interest and calibration of associated analyte detection systems.

SUMMARY

In accordance with various embodiments further discussed herein, calibration systems and methods are provided for analyte detection systems. For example, an analyte detection system may include a detection device and a calibration device that may be releasably attached, permanently attached, or integrated therewith. A chamber of the calibration device may receive a sample for examination (e.g., also referred to as a sample under examination, material for examination, material under evaluation) which may be sampling media (e.g., used for in field detection operations) or a calibrant reservoir storing a known calibrant (e.g., used for in field calibration operations). The sampling media may be implemented using an appropriate substrate such as polytetrafluoroethylene (PTFE), an aramid polymer, polyethylene, polyester, paper, and/or other materials. In some cases, a calibrant may be provided in the calibrant reservoir in solid form, gel form, or liquid form. For example, the calibrant reservoir may include mesh features, such as a gas permeable membrane, disposed over a calibrant (e.g., solid, gel, liquid), in which at least partially vaporized calibrant (e.g., obtained from heating and/or blowing air through the calibrant) can pass. In some cases, the calibrant reservoir may include a flushing agent (e.g., acetone, toluene, water, mixture thereof) to clean out the calibrant reservoir and/or detection device. For example, the flushing agent may flush out or revitalize the calibrant reservoir and/or detection device.

In some embodiments, a heater of the calibration device may heat the sample, which may include analytes, disposed in the chamber to at least partially vaporize the sample to provide vaporized portions of the sample, which may include analytes (e.g., vaporized analytes), to an analyte detector of the detection device. The analytes are, or include, materials responsive to one or more analyte reporters of the analyte detector. In some embodiments, portions of the sample may be provided without a heater. A pump(s) and/or a fan(s) of the calibration device and/or detection device may be used to pull air or push air, respectively, through or over the sample to provide at least a portion of the sample to the analyte detector. In some embodiments, such pump(s) and/or fan(s) may be used alternative to and/or in addition to a heater(s) for providing the portion of the sample.

In some embodiments, the analyte detector may be provided as one or more materials that can be provided directly to the calibration device to receive a sample for examination (e.g., a calibrant). For instance, the analyte detector may be an object (e.g., piece of paper) coated with material responsive to the sample.

When the sample for examination is sampling media, the sampling media includes test samples. At least a portion of the test samples is provided (e.g., in vaporized or particulate form) to the analyte detector. Analyte reporters of the analyte detector may be exposed to the portion of the test samples. When the test samples include appropriate analytes, one or more analyte reporters of the analyte detector may exhibit a response to one or more of the analytes. The presence of a response of the analyte reporter is indicative of one or more materials of interest associated with the analytes being present in the test samples. By way of non-limiting example, materials of interest may include explosives, narcotics, biological materials, biological and/or chemical warfare agents, toxic industrial chemicals (TICs), illicit substances, and others as appropriate.

When the sample for examination is a calibrant reservoir, a calibrant stored therein may be used to determine whether the analyte reporters are operating properly. Multiple calibrant reservoirs may be cycled through to test the analyte reporters. The analyte detector may be selectively calibrated based on test results obtained by exposing the analyte reporters to one or more calibrants.

In one or more embodiments, a system includes a calibration device configured to operate with an analyte detector (e.g., of a detection device). The calibration device includes a chamber configured to receive a sample and pass at least a portion of the sample including analytes to the analyte detector for examination. The calibration device further includes a reservoir including a calibrant and configured to be selectively positioned in the chamber as the sample to provide the portion of the sample including the analytes to calibrate the analyte detector. In some embodiments, the system further includes a sample extraction component configured to provide (e.g., propel) at least a portion of the sample for examination from the chamber to the analyte detector. The sample extraction component may include a heater configured to heat the sample to at least partially vaporize the sample to provide the analytes. Alternatively and/or in addition, the sample extraction component may include a pump and/or a fan to apply air through or over the sample (e.g., apply air through the heated sample in the case that the sample is heated) to provide the analytes. The sample extraction component may include one or more associated actuators to position the heaters, pumps, and/or fans as appropriate to provide the portion of the sample to the analyte detector.

In one or more embodiments, a method includes initiating a calibration operation to calibrate an analyte detector. The method further includes positioning a reservoir in a chamber of a calibration device in response to the initiating. The reservoir includes a calibrant. The method further includes providing at least a portion of the calibrant including analytes associated with the calibrant to the analyte detector. The method further includes detecting a response of the analyte detector to the analytes. The method further includes determining whether the analyte detector is operating properly based at least on the detected response.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
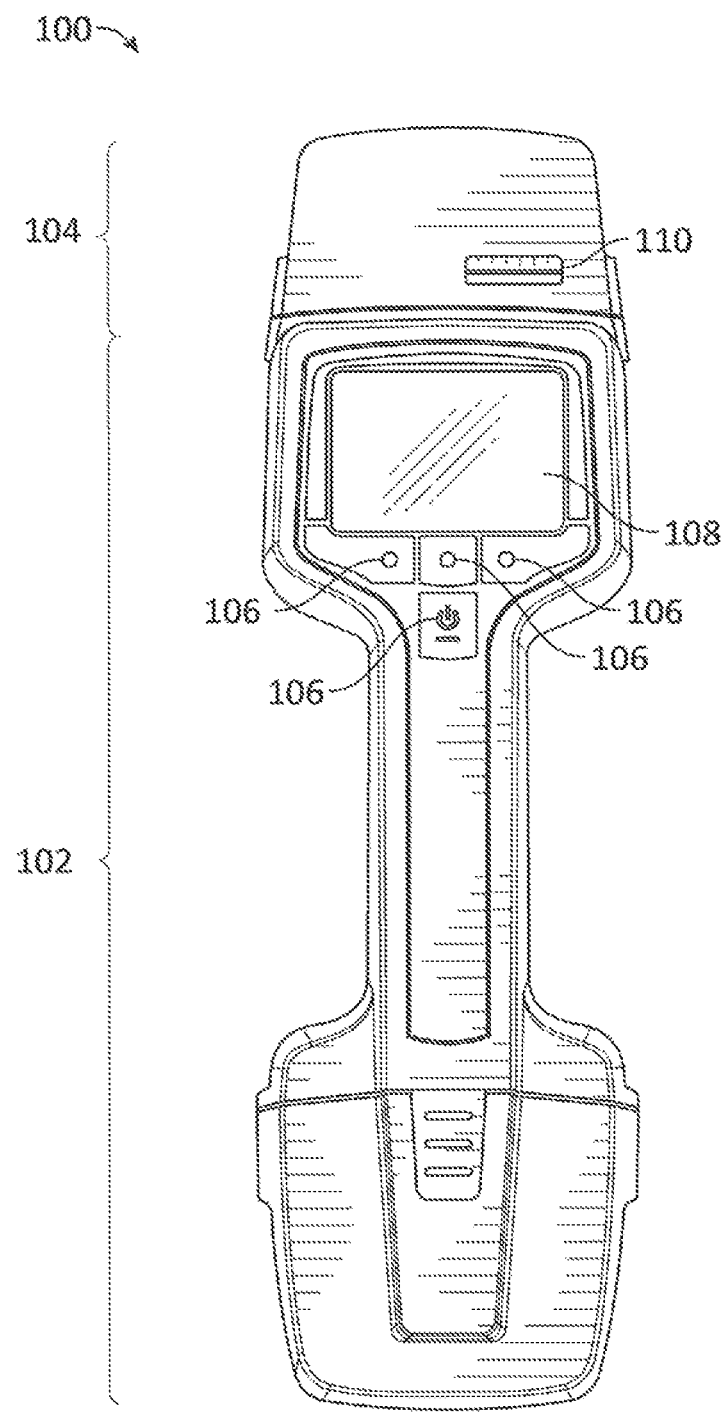
FIG. 1 illustrates an external view of a system including a detection device and an attached calibration device in accordance with an embodiment of the disclosure.

Various techniques are provided herein to facilitate calibration of analyte detection systems. Such analyte detection systems may be operated to detect the presence of materials of interest based on detection and analysis of analytes (e.g., vapor-phase analytes) that may be in test samples. By way of non-limiting example, materials of interest may include explosives, narcotics, biological materials, biological and/or chemical warfare agents, TICs, illicit substances, and others as appropriate.

In an embodiment, an analyte detection system (e.g., also referred to simply as a detection system or a system) includes a detection device and a calibration device. The detection device may include an inlet, an analyte detector, an outlet, and a pump. The inlet may be used to receive and pass analytes (e.g., included in test samples), such as from the calibration device. Dependent on application, the analytes may be solid-phase material, vapor-phase material, particulates (e.g., dust), and/or other material received by and transported the inlet (e.g., using air pushed by a fan(s) and/or pulled by a pump(s)). For example, in some cases, the test samples may be heated to provide at least a portion of the test sample in a vapor-phase to the inlet. A pump may be used to pull air (e.g., including any analytes) into the inlet, through the inlet and analyte detector, and out the outlet. In some cases, the portion of the test sample, which may include analytes, may propagate through the inlet and to the analyte detector without a pump or a fan.

The analyte detector may include one or more analyte reporters and associated response detector(s). In some cases, the analyte reporters may be referred to as sensing channels of the analyte detector. Each analyte reporter is capable of responding to (e.g., reacting to) one or more materials of interest (e.g., explosives, narcotics, and/or other chemical and/or biological materials) that may be present in the analytes when the analyte reporter is exposed to the analytes. In this regard, the analyte detector may be implemented as a chemical detector, particulate detector, biological material detector, and/or generally any detector capable of detecting one or more materials of interest. A response or lack of response of the analyte reporter to the analytes may be used to detect the presence or lack of presence of materials of interest in the analytes. For example, an analyte reporter may include a peroxide-reactive compound that can react to peroxide-based explosives (or components thereof) in the analytes, with detection of such reaction being an indication of presence of peroxide-based explosives in the analytes.

A response of the analyte reporter to the analytes may be detected (e.g., captured, measured) by a corresponding response detector. In an embodiment, when exposed to a material of interest, the analyte reporter may produce a fluorescent response, a change in fluorescence, a luminescent response, a change in luminescence, a change in electrical properties (e.g., conductivity, resistivity, and/or other properties), and/or a colorimetric response (e.g., change in the analyte reporter's color) that can be detected by the response detector, e.g. relative to a case in which the analyte reporter is not exposed to the material of interest. The response detected by a response detector may be referred to as response data. The response data and/or information (e.g., statistics) associated with the response data may be provided to and/or derived at least in part by the detection system. For example, the response data and/or associated information may be provided to and/or derived by a processor of the detection device.

The analyte detector may be implemented as a mass spectrometer (MS), an ion mobility spectrometer (IMS), a fluorescence-based detector, a colorimetric detector, an electrical-based detector, and/or using other technologies, including those that use a swipe-based thermal desorber to perform material detection as further discussed herein. For example, the electrical-based detector may be a detector configured to detect changes in electrical properties, such as changes in conductivity, resistivity, voltage, current, electromagnetic field, and/or other properties, of the analyte reporter when the analyte reporter is exposed to the material of interest. The various technologies may be used with or without heaters and/or with or without pumps and/or fans.

The calibration device includes a chamber and one or more calibrant reservoirs. The calibration device may be releasably attached, permanently attached, or integrated with the detection device. For example, in an embodiment, the calibration device may be an accessory (e.g., also referred to as an attachment, a modular attachment) that can be releasably attached, permanently attached, or integrated with the detection device. The chamber is configured to receive a sample for examination. At least a portion of the sample may be provided to the inlet of the detection device.

In some embodiments, the system may include a sample extraction component to provide at least a portion of the sample to the analyte detector. In this regard, one or more components of the sample extraction component may be included in the calibration device and/or the detection device. The sample extraction component may include a heater configured to heat the sample to provide completely or partially vaporized sample to the analyte detector of the detection device (e.g., via the inlet). Alternatively or in addition, the sample extraction component may include a fan and/or a pump to push or pull the sample to provide at least a portion of the sample to the analyte detector. The sample extraction component may also include one or more actuators to move associated heaters, fans, pumps, and/or calibrant reservoir (e.g., via translational and/or rotational movement) as appropriate to position the sample in the chamber and/or to provide at least a portion of the sample to the analyte detector.

In an embodiment, the analyte detection system may be used to perform normal operation (e.g., also referred to as analyte detection operation or non-calibration operation) or a calibration operation (e.g., also referred to as an evaluation operation). In an embodiment, in normal operation, sampling media including test samples may be inserted through a slot and into the chamber of the calibration device. In this case, the sample for examination may refer to the sampling media and/or the test samples. In some cases, the sampling media is heated (e.g., by a heater(s) of the calibration device) to at least partially vaporize the test samples and provide at least a portion of the at least partially vaporized test samples to the analyte detector. Analytes may be included in the portion provided to the analyte detector. In these cases, the heater may be moved to contact the sampling media. In other cases, air is pushed through or pulled through the sampling media, such as by a fan(s) or a pump(s) of the calibration device, respectively, to provide the portion of the sample (e.g., in vaporized or particulate form) to the analyte detector. The analyte detector can determine whether materials of interest are present in the test samples, e.g. based on a response of one or more analyte reporters to analytes included in the test samples as detected by one or more response detectors.

In an embodiment, in normal operation, use of the sampling media may not be necessary, as the inlet may be used to directly sample ambient air to provide vapor-phase analytes to the analyte detector. For example, the calibration device may be detached from the detection device such that the inlet of the detection device is exposed to the ambient air. Additional devices (e.g., coupled to or part of the calibration device and/or detection device) may be used to direct the sampled ambient air, which may include analytes, into the inlet, such as an air filter/concentrator positioned in the flow path of the sampled ambient air. Thus, in some embodiments, in normal operation, a detection process may be performed on the inserted sampling media or by sampling ambient air to determine whether or not one or more materials of interest are present.

In some embodiments, a calibration operation is performed on analyte reporters to determine whether each analyte reporter is operating properly. In this regard, in a calibration operation, one or more of the analyte reporters of the analyte detector may be tested using calibrants. In this regard, a calibrant contained in each calibrant reservoir may be used to elicit (or not elicit) a response from the analyte reporters. A calibrant refers to a known substance whose response to the analyte reporters are known. For example, the calibrant may include a known amount (e.g., known concentration) of one or more materials of interest. The calibrant may be used to test an analyte reporter's ability to detect presence or lack of presence of certain materials of interest.

During a calibration operation, the chamber receives a calibrant reservoir. In this case, the sample for examination may refer to the calibrant reservoir and/or the calibrant stored by the calibrant reservoir. With the calibrant reservoir disposed in the chamber, the heater heats the calibrant reservoir to provide vaporized calibrant to the analyte detector. The vaporized calibrant may be, or may include, analytes responsive to one or more analyte reporters of the analyte detector. In some cases, the heater may be moved to contact the calibrant reservoir. The response detector(s) of the analyte detector can detect the response of the analyte reporter(s) to the calibrant. Thus, in a calibration operation, a test process is performed on calibrant reservoirs in order to test the analyte reporters. A calibration operation may include cycling through all the calibrant reservoirs, a subset of the calibrant reservoirs, and/or generally any desired combination of calibrant reservoirs. In an embodiment, the calibrant reservoirs may be provided by a calibrant wheel that can be rotated to selectively position one of the calibrant reservoirs in the chamber.

For exposure of a given analyte reporter to a calibrant, the response of the analyte reporter to the calibrant that is detected by the response detector(s) of the analyte detector may be compared with an expected response to determine whether the analyte reporter is operating properly. In an embodiment, when exposed to a material of interest in the calibrant to which the analyte reporter is responsive, the analyte reporter may produce a fluorescent response, a change in fluorescence, a luminescent response, a change in luminescence, a change in resistivity, a change in electrical properties, a colorimetric response, and/or other responses that can be detected by the response detector.

For each analyte reporter that is tested, the detection system may determine whether the analyte reporter is operating properly based on responses detected by the corresponding response detector. Such responses may be, or may be used to derive, results of the calibration operation with respect to the analyte reporter. In some cases, a processor of the detection device can be used to make the determination based on the responses detected by the corresponding response detector.

The detection system may perform one or more actions based on whether the analyte reporter is determined to be operating properly. When the results indicate that the analyte reporter is not operating properly and/or is providing inconsistent results, such results may indicate that the analyte reporter may need to be replaced. An analyte reporter may be determined to be operating properly when an expected response exhibited by the analyte reporter is within a threshold of a measured response exhibited by the analyte reporter. In this regard, the threshold being exceeded may serve as a trigger that the analyte reporter is not operating properly. A replacement of the analyte reporter with another analyte reporter (e.g., of a similar or same composition) may be considered a calibration of the analyte detector.

As an example, a response detector may be, may include, or may be a part of, a fluorescence-based detector that measures fluorescence signals emitted by the analyte reporter when the analyte reporter is exposed to the analytes. The processor may make a determination that the analyte reporter is not operating properly when the fluorescence signals detected by the response detector are too bright, too dim, or otherwise sufficiently different (e.g., different beyond a predetermined threshold intensity) from an expected fluorescence response; otherwise, the processor may make a determination that the analyte reporter is operating properly. As another example, a response detector may be, may include, or may be a part of, an electrical-based detector that measures a conductivity of the analyte detector. The processor may make a determination that the analyte reporter is not operating properly when the conductivity measured by the response detector is too small or too large relative to an expected conductivity; otherwise, the processor may make a determination that the analyte reporter is operating properly. In some cases, when the response detector measures no response, the calibrant reservoir may be determined to be empty.

In cases that the response data deviates inconsistently and/or greatly from expected results, the processor may provide an indication (e.g., notification) to a user (e.g., via a display, a light emitting diode (LED) indicating error, etc.) regarding the error and/or identifying the components (e.g., analyte reporters) of the detection system that may require maintenance, replacement, and/or further analysis. For example, the detection system may include, and/or may be coupled to, a display or other audio and/or visual device to provide an indication to a user of the detection system of which analyte reporter(s) is operating properly and/or which analyte reporter(s) is not operating properly. In some cases, the detection system may provide a suggested course(s) of action to the user (e.g., based on a type or magnitude of error detected by the detection system). In this manner, the user may take corrective action, such as performing additional tests on analyte reporter(s) and/or removing or replacing analyte reporter(s) determined to not be operating properly, or the changes can be automated depending on the detection device's capabilities.

In some cases, when an analyte reporter is determined not to be operating properly, the analyte reporter may be replaced (e.g., manually or automated replaced) with another analyte reporter (e.g., of similar or same nominal properties as the analyte reporter being replaced). The replacement analyte reporter may need to be conditioned, such as being placed and left alone in the analyte detector for a certain amount of time (e.g., 5 seconds to 90 seconds for some analyte reporters), before being used. In some cases, after the conditioning (if needed), the replacement analyte reporter may be tested in a calibration operation.

In some embodiments, the analyte detector may be selectively calibrated in response to results of a calibration operation. In some cases, the analyte detector (e.g., some or all of the analyte reporters) may be retested in a calibration operation subsequent to the calibration of the analyte detector. In some cases, when the analyte reporters are determined to operate properly, no calibration is performed (e.g., no adjustments to the analyte detector are made).

In some cases, when the processor determines that the response data provided by a certain response detector is consistently off (e.g., by a certain amount), the processor may cause adjustment of the response data provided by the response detector to better conform the response data to expected results. For example, the processor may receive response data from the response detector and adjust the response data by applying an offset. In this example, the processor may apply an offset to any response data received from the response detector when the response detector is consistently off by the offset.

As another example, alternatively and/or in addition, based on the detected response, the processor may provide control signals to the response detector to cause the response detector to adjust response data being provided by the response detector to calibrate the response detector. In this example, the processor may adjust or cause the response detector to adjust a setting of the response detector, such as a responsivity, a sensitivity, a response data range (e.g., maximum input and/or output levels), an applied offset, and/or other parameters associated with obtaining and/or deriving response data.

In some embodiments, one or more of the calibrant reservoirs (e.g., provided by a calibrant wheel) contain no calibrant and have no vent. Such a calibrant reservoir may implement and may be referred to a sealing member. In some cases, a surface of the sealing member may be pushed against an inlet associated with an analyte detector, and a flow or pressure sensor (e.g., within the analyte detector) may be used to check for leaks. In this regard, the sealing member may be positioned in the chamber of the calibration device to check for leaks downstream of the inlet (e.g., leaks in an analyte detector or route therebetween).

In some cases, a calibration operation may be manually initiated by a user of the detection system. Alternatively and/or in addition, a calibration operation may be initiated when one or more criteria have been satisfied. One example criterion may be a number of sampling media that have been inserted in the accessory and analyzed. For example, a calibration operation may be autonomously initiated by the processor of the trace materials detection device after the analyte detection system has been used to perform a detection process a pre-set number of sampling media. Another example criterion may be an amount of time that has passed since a previous calibration operation and/or since the detection system has been used. Other example criteria may include receiving particularly high readings, particularly low readings, and/or generally unexpected readings (e.g., relative to expected readings) associated with one or more of the analyte reporters. For example, in some cases, a particularly high reading provided by a response detector may cause subsequent readings by the response detector and/or other response detectors of the analyte detector to read higher.

In an embodiment, the calibration device may include a barrier (e.g., also referred to as a blocker or blocking member) to selectively block the slot of the calibration or sampling device in order to prevent entry/insertion of material (e.g., sampling media, ambient air) into the calibration device (e.g., into the chamber of the calibration device) via the slot during a calibration operation. For example, the barrier may be or may include a physical solenoid door. Any material that enters the calibration device may contaminate or otherwise affect the results from the calibration operation. In some cases, the barrier can block the slot when the calibration device is not in use (e.g., not used to normal or calibration operation) to reduce maintenance costs and resources associated with removing any material that enters the chamber or otherwise cleaning the chamber.

A calibration operation may be used to reduce errors associated with detecting and classifying materials of interest. Errors may include false positives, in which a material of interest is determined to be present in a sample for examination when in actuality the material of interest is not present, and false negatives, in which a material of interest is determined not to be present on the sample when in actuality the material of interest is present. In some cases, based on an analysis of calibration responses (e.g., by the processor), the processor may adjust or cause adjustment of parameters used for material detection and classification such that detection and/or classification results are generally improved. For example, if an analyte reporter responds well (e.g., as expected) to a calibrant in terms of response magnitude but is slower to respond than expected, this data can be used to adjust the parameters used to determine if a material of interest (e.g., a threat) is detected in a sample for examination and/or classify the material of interest.

In an embodiment, the user of the detection system may set the criterion or criteria that cause a calibration operation to be initiated and/or define a calibration operation. For example, a definition of a calibration operation may identify the calibrant reservoir(s) to be used in the operation, an order in which to use the calibrant reservoirs, and/or other parameters (e.g., temperatures from heaters, suction pressure from pump) used in the calibration operation. The processor may determine whether any criterion that triggers initiation of a calibration operation has occurred, and initiate a calibration operation accordingly. In an embodiment, the processor may be provided with autonomy to set the criterion or criteria and/or define a calibration operation. In such an embodiment, no or minimal user intervention may be needed, e.g. after an initial setup of the detection system by the user. In some cases, the processor may request authorization to initiate a calibration operation defined by the processor (e.g., and provide information regarding rationale for performing the calibration operation), and proceed with initiating the calibration operation if authorization is received.

In an embodiment, existing library of known or expected responses associated with materials of interest can be used to analyze response data provided by response detectors. For example, intensities of light emitted by exposure of an analyte reporter to the analytes may be analyzed by comparing the detected intensities to expected intensities. The comparison can be used during normal operation to determine whether materials of interest are present and/or used during a calibration operation to evaluate and selectively calibrate the analyte detector.

Although the foregoing is described in relation to operation of the calibration device with the detection device, in an embodiment, the calibration device may be operated as a standalone calibration and/or detection device (e.g., independent of the detection device). The calibration device may contain a power source (e.g., battery) and/or connection thereto (e.g., a wired connection to an outlet). As examples, in this embodiment, the testing sample may be placed in the chamber of the calibration device or placed in proximity to or in contact with a calibrant reservoir (e.g., the testing sample is pushed by a user on the calibrant reservoir). A pump(s) and/or fan(s) of the calibration device may be used to blow out a calibrant (e.g., simulant) contained in the calibrant reservoir onto the testing sample. The pump(s) and/or fan(s) may be used with or without a heater(s) and/or with or without an inlet.

When the testing sample contains one or more materials of interest that react to the calibrant, the testing sample may exhibit a change in electrical properties (e.g., conductivity, resistivity, etc.), a colorimetric response (e.g., change in color), and/or other changes. Such changes may be detected by human inspection, such as a change in color of the testing sample (e.g., litmus paper), or additional equipment, such as a multimeter to measure electrical properties of the testing sample. In this manner, the calibration may be used to test the testing sample and/or the calibrants contained in the calibrant reservoirs.

As an example, in this embodiment, the analyte detector may be one or more reactive materials provided directly to the calibration device. For instance, the analyte detector may be an object (e.g., piece of paper) coated with material appropriate for responding to a sample for examination. A calibrant reservoir may be provided in the chamber as the sample. In one case, the piece of material can be placed in the chamber and pushed against the calibrant reservoir (e.g., by a user's hand, by an actuator) to allow the piece of material to be exposed to the calibrant. In another case, the piece of material can be pushed against an orifice (e.g., implemented in the same or similar fashion as an inlet 202 shown in FIG. 2) that provides calibrant from the calibrant reservoir to the piece of material. In some cases, an inlet may be implemented as part of the calibration device to receive and pass through a calibrant. The calibrant reservoir may be, but need not be, heated (e.g., depending on calibrant). One or more properties of the piece of material (e.g., color of the piece of material) may change when exposed to a properly operating calibrant. A calibration operation may be performed to determine whether the piece of material and/or a calibrant(s) is operating properly.

Thus, using various embodiments, the detection system may be utilized for chemical detection through desorption of test samples or known calibrants. The detection system may provide detection of materials of interest in test samples and evaluation and selective calibration of the chemical detector in a low cost, rapid, and highly portable manner. In general, no additional substances, equipment, and/or setup need to be provided at the time of calibration, with components for normal operation (e.g., using test samples) and calibration operations (e.g., using calibrants) already being integrated in the detection system. Transitioning from normal operation to a calibration operation, or vice versa, is streamlined.

In some embodiments, few or no user interactions are required to transition from these operations. For instance, in some cases, once a calibration operation is initiated, user interaction may be needed to remove any sampling media in the chamber of the calibration device, after which the calibration operation can be performed autonomously by the detection system with minimal or no user interaction. In this regard, the calibrant reservoirs may be disposed in the chamber and used to provide analytes (e.g., by heating and/or passing air through or over the calibrant reservoirs) with minimal or no user interaction. In an embodiment, the health of any or all of the detection system's analyte reporters may be determined using different calibrant sources to gather feedback from the analyte reporters. Reduced user interaction may have an associated reduction in user errors, such as those related to incorrect manual insertion of verification samples by the user in conventional systems.

Figure 2:
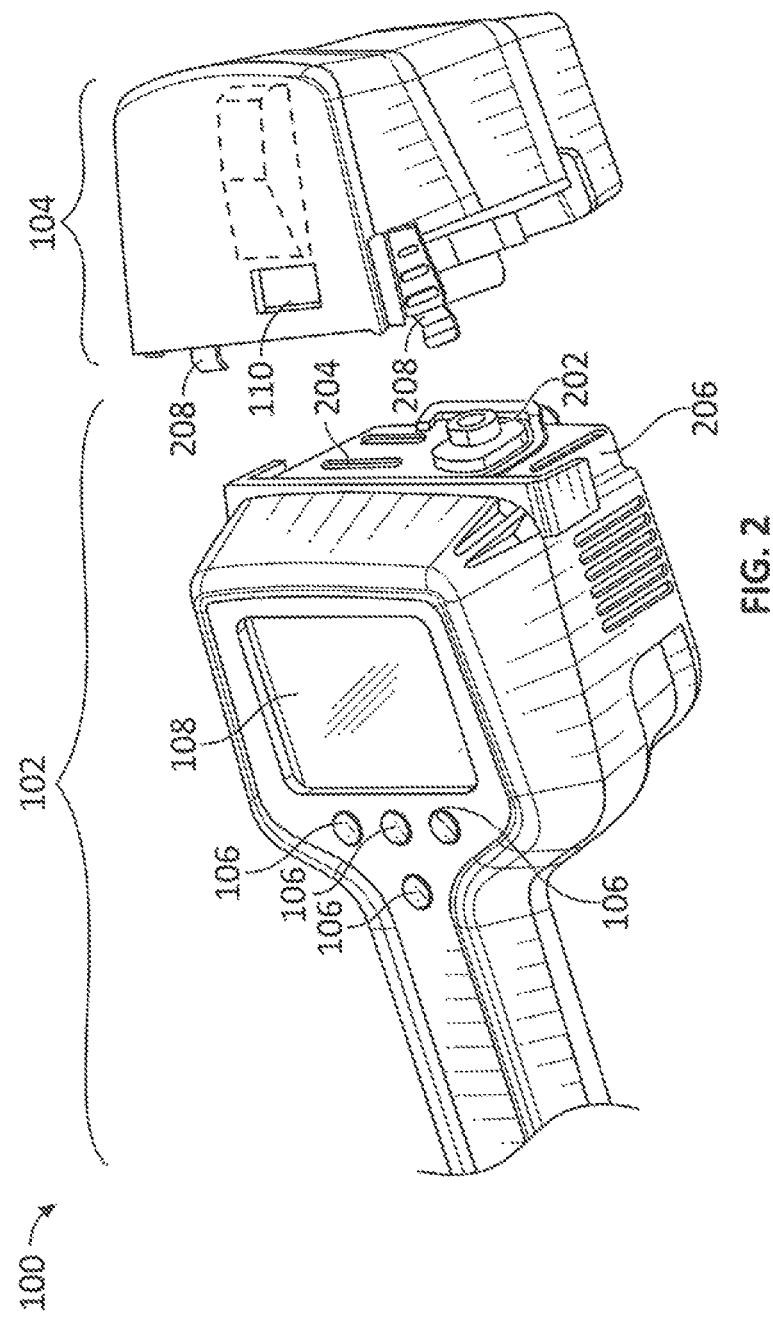
FIG. 2 illustrates an external view of a system including a detection device and a detached calibration device in accordance with an embodiment of the disclosure.

Turning now to the drawings, FIG. 1 illustrates an external view of a system 100 (e.g., also referred to as an analyte detection system or detection system) including a detection device 102 and an attached calibration device 104 in accordance with an embodiment of the disclosure. FIG. 2 illustrates an external view of the system 100 including a detection device 102 and a detached calibration device 104. For example, in some embodiments, the system 100 may be implemented as a handheld portable detection system capable of detecting explosives, narcotics, and/or other biological and/or chemical materials.

As shown, the system 100 includes a detection device 102 and a calibration device 104 releasably attached to the detection device 102. The calibration device 104 is shown attached to the detection device 102 in FIG. 1, and detached from the detection device 102 in FIG. 2. In other embodiments, the calibration device 104 may be permanently attached or integrated with the detection device 102. In some embodiments, the calibration device 104 may be provided as an accessory, an attachment, or a modular attachment of the detection device 102. In some embodiments, the calibration device 104 may be used as a standalone device (e.g., independent of the detection device 102).

The detection device 102 includes user controls 106 and a display 108. The user controls 106 receive user input to operate the system 100. As shown in FIG. 1, the user controls 106 may be implemented as physical buttons. In other embodiments, the user controls 106 may be implemented by one or more keyboards, levers, joysticks, touchscreens, and/or other controls. In some embodiments, the user controls 106 may be integrated with the display 108 as a touchscreen. In an embodiment, the user controls 106 may be used by the user to set the system 100 in normal operation or a calibration operation. In some cases, the user may use the user controls 106 to provide inputs for defining a calibration operation.

The display 108 presents information to the user of the system 100. In various embodiments, the display 108 may be implemented as a liquid crystal display (LCD), an organic light emitting diode (OLED) display, and/or any other appropriate display. In an embodiment, the display 108 may display response data, alerts, authorization requests, and/or generally any feedback to the user that may, but need not, involve user interaction. For example, during a calibration operation, the display 108 may indicate a status of a pending calibration operation (e.g., current calibrant reservoir in chamber), associated response data and/or expected data, potential errors (e.g., chemical detector is not operating properly, sampling media is in chamber and needs to be removed), and/or other information or prompts. As another example, the display 108 may include an authorization request to initiate a calibration operation. The user may respond to the authorization request and/or other prompts using the user controls 106.

The calibration device 104 includes a slot 110. In normal operation of the system 100, sampling media may be brought into physical contact with one or more surfaces to be tested. For example, in some embodiments, the user may wipe the sampling media (e.g., also referred to as a sampling swab, sampling swipe, or sampling medium) against a surface of interest to collect trace amounts of one or more test substances resident on the surface. The test surface may be a surface of a package, a luggage, clothing, or other article. The user then inserts the sampling media through the slot 110 and into a chamber of the calibration device 104 after which additional operations and analysis are performed as further discussed herein. In some embodiments, the sampling media may be implemented using an appropriate substrate such as PTFE, an aramid polymer, polyethylene, polyester, paper, and/or other materials. In a calibration operation of the system 100, a calibration reservoir may be disposed in the chamber of the calibration device 104 after which additional operations and analysis are performed as further discussed herein. In some cases, the calibration device 104 may include a barrier to selectively block the slot 110 to prevent sampling media, ambient air, and generally any material from entering the calibration device 104 (e.g., during a calibration operation).

In some embodiments, use of the sampling media may not be necessary, as an inlet (e.g., of the detection device 102 and/or the calibration device 104) may be used to directly sample ambient air for vapor-phase analytes. In some cases, the sampled ambient air, which may include vapor-phase analytes, may be provided to the inlet via the slot 110 of the calibration device 104. Additional devices may be used to direct the sampled ambient air into the inlet, such as an air filter/concentrator positioned in the flow path of the sampled ambient air.

As shown in FIG. 2, the detection device 102 includes an inlet 202, an electrical interface 204, and engagement slots 206 (e.g., also referred to as engagement apertures or engagement structures). The inlet 202 samples ambient air for analytes (e.g., by receiving and/or drawing in ambient air). The sampled ambient air may include solid-phase material, vapor-phase material, particulates (e.g., dust), and/or other material received by the inlet 202. The electrical interface 204 includes electrical connections for providing power and control signals. For example, the electrical interface 204 includes power and ground pins for providing power and communication pin(s) for providing control signals. In an embodiment, the electrical interface 204 provides power and control signals to the calibration device 104 when the calibration device 104 is attached to the detection device 102.

The calibration device 104 may be releasably attached to the detection device 102 at least by engaging spring-loaded tabs 208 of the calibration device 104 to the corresponding engagement slots 206 of the detection device 102. Alternatively and/or in addition, the calibration device 104 and the detection device 102 may be releasably attached by other means in other embodiments.

In operation, when the calibration device 104 is attached to the detection device 102 (e.g., as shown in FIG. 1), the detection device 102 may provide power and control signals to the calibration device 104 via the electrical interface 204. In some cases, the calibration device 104 includes a corresponding electrical interface (not shown in FIGS. 1 and 2) to couple to the electrical interface 204 of the detection device 102 and receive the power and control signals from the electrical interface 204. The inlet 202 of the detection device 102 may receive test samples, which may include analytes, provided by the calibration device 104.

In various embodiments, additional components of the system 100 (e.g., further illustrated in FIG. 3 and other figures) may be distributed at physical locations internal to and/or external to corresponding housings and/or covers of the detection device 102 and calibration device 104. Additional features of the system 100 in accordance with an embodiment are further illustrated in FIG. 3. It is noted that not all of the depicted components may be required, however, and one or more embodiments may include additional components not shown in FIG. 3. Variations in the arrangement and type of the components may be made without departing from the spirit or scope of the claims as set forth herein. Additional, fewer, and/or different components may be provided. For example, in some embodiments, pump 314 and/or heaters 316 of the detection device 102 may be optional, and/or heater 336 and heater actuator 338 of the calibration device 104 may be optional.

Figure 3:
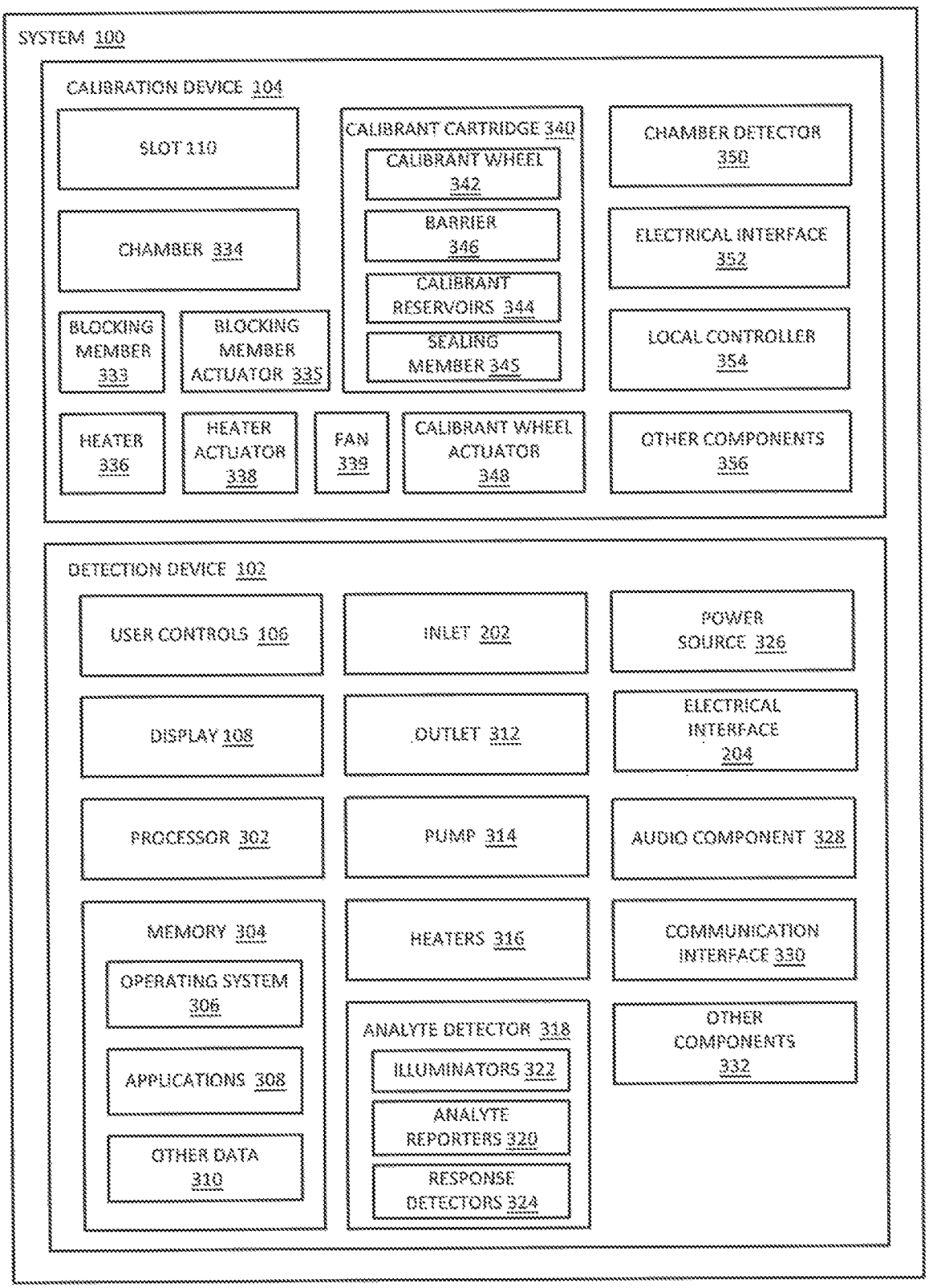
FIG. 3 illustrates a block diagram of a system in accordance with an embodiment of the disclosure.

FIG. 3 illustrates a block diagram of the system 100 in accordance with an embodiment of the disclosure. In addition to several previously discussed components shown in FIGS. 1 and 2, the detection device 102 also includes a processor 302, a memory 304, an outlet 312, a pump 314, heaters 316, an analyte detector 318, a power source 326, an audio component 328, a communication interface 330, and other components 332.

The processor 302 may be implemented as one or more microprocessors, microcontrollers, system on a chip (SoC), application specific integrated circuits (ASICs), programmable logic devices (PLDs) (e.g., field programmable gate arrays (FPGAs), complex programmable logic devices (CPLDs), field programmable systems on a chip (FPSCs), or other types of programmable devices), or other processing devices used to control the operations of the detection device 102. In some cases, the processor 302 may also control the operations of the calibration device 104, such as when the calibration device 104 is attached to the detection device 102. In this regard, processor 302 may execute machine readable instructions (e.g., software, firmware, or other instructions) stored in memory 304. The processor 302 may generate control signals for the various components of the detection device (e.g., heaters 316, analyte detector 318) and/or various components of the calibration device 104.

In an embodiment, the processor 302 may generate control signals to transition the calibration device 104 from normal operation to a calibration operation. In some cases, the processor 302 may be provided with autonomy to set the criterion or criteria to initiate a calibration operation and/or autonomy to define a calibration operation.

For each analyte reporter 320 that is tested, the processor 302 may determine whether the analyte reporter 320 is operating properly based on responses detected by the corresponding response detector. Such responses may be, or may be used to derive, results of the calibration operation with respect to the analyte reporter 320. For example, the processor 302 may determine that an analyte reporter 320 is operating properly when an expected response exhibited by the analyte reporter 320 is within a threshold of a measured response exhibited by the analyte reporter 320. The processor 302 may perform one or more actions based on whether the analyte reporter is determined to be operating properly. When the results indicate that an analyte reporter 320 is not operating properly and/or is providing inconsistent results, such results may indicate that the analyte reporter 320 may need to be replaced.

In cases that the response data from the response detectors 324 deviate inconsistently and/or greatly from expected results, the processor 302 may provide an indication to a user (e.g., via the display 108) regarding the error(s) and/or identifying the component(s) (e.g., analyte reporter(s)) of the system 100 that may require maintenance, replacement, and/or further analysis. The display 108 may provide an indication to the user of which of the analyte reporters 320 are operating properly and/or which are not operating properly. In some cases, the processor 302 may provide for display in the display 108 a suggested course(s) of action to the user (e.g., based on a type or magnitude of error detected by the processor 302). The user may take corrective action, such as performing additional tests on one or more of the analyte reporters 320 and/or removing or replacing the analyte reporters 320 determined to not be operating properly or automated based on the response. In some cases, when the response detector measures no response, the calibrant reservoir 344 may be determined to be empty.

In some cases, when an analyte reporter 320 is determined not to operate properly, the analyte reporter 320 may be replaced with another analyte reporter (e.g., of similar or same nominal properties as the analyte reporter being replaced). The replacement analyte reporter may need to be conditioned, such as being placed and left alone in the analyte detector for a certain amount of time (e.g., 5 seconds to 90 seconds for some analyte reporters), before being used. In some cases, after the conditioning (if needed), the replacement analyte reporter may be tested in a calibration operation.

In an embodiment, alternatively and/or in addition to identifying and indicating errors to the user, the processor 302 may determine whether to calibrate the analyte detector 318 based on the response data provided by the response detectors 324. In some cases, the processor 302 may adjust response data received from a response detector 324, such as by applying an offset, to calibrate the response detector 324. In some cases, the processor 302 may provide control signals to a response detector 324 to cause the response detector 324 to adjust response data being provided by the response detector 324 to calibrate the response detector 324, such as by adjusting or causing the response detector 324 to adjust a setting (e.g., responsivity, sensitivity) of the response detector 324. In some cases, the analyte detector 318 (e.g., some or all of the analyte reporters 320) may be retested in a calibration operation subsequent to the calibration of the analyte detector 318.

The memory 304 may be implemented as a machine readable medium storing various machine readable instructions and data. For example, in some embodiments, the memory 304 may store an operating system 306 and one or more applications 308 as machine readable instructions that may be read and executed by the processor 302 to perform various operations described herein. The processor 302 may utilize the applications 308 to generate control signals and present detection results during normal and/or calibration operation of the system 100. The memory 304 may store various types of data 310 including, for example, profiles of various materials (e.g., test samples, calibrants, analyte reporters), which calibrant reservoirs contain which calibrants, calibration results, test sample identification results, and/or other information used or provided by the various components of the system 100.

In an embodiment, the data 310 may include information from materials handbooks. The information may include material properties, such as composition, vapor pressure, melting point, condensation point, vaporization point, desorption temperature, desorption rate, and/or other information for various materials. The information may be used as reference by the user and/or one or more of the applications 308 to facilitate analyte detection by the analyte detector 318 and/or evaluation/calibration of the analyte detector 318. The memory 304 may store the materials handbooks themselves and/or may store information (e.g., links, access information, etc.) to access the materials handbooks (e.g., online or cloud sources).

In an embodiment, the memory 304 may store information pertaining to expected responses when certain analyte reporters are exposed to certain materials. As an example, for some combination of analyte reporter and sample for examination, the exposure of the analyte reporter to the material may cause the analyte reporter to produce a fluorescent response, a change in fluorescence, a luminescent response, a change in luminescence, a change in electrical properties, a colorimetric response, and/or other responses. Comparisons between expected results (e.g., determined from equations/relations) and actual results (e.g., obtained from empirical response data) may be utilized for calibration of the analyte detector 318. In some cases, such comparisons may be performed by the processor 302. The memory 304 may also store calibration results.

In various embodiments, the memory 304 may be implemented to store such instructions and data in a non-transitory manner and/or may be implemented with both transitory and non-transitory portions to selectively store all or portions of such instructions and data in either manner as appropriate. In an embodiment, the memory 304 may be implemented as non-volatile memory (e.g., flash memory, hard drive, solid state drive, or other non-transitory machine readable mediums), volatile memory (e.g., random access memory), or combinations thereof.

The inlet 202, outlet 312, pump 314, and analyte detector 318 may be used with the heaters 316 to provide a swipe-based thermal desorber to perform material detection (e.g., vapor-based material detection) as further discussed herein. In this regard, test samples, which may include analytes, may be drawn into the inlet 202, through the analyte detector 318, and out of the outlet 312 using the pump 314. In some embodiments, the inlet 202 can directly sample ambient air for analytes without the need for the swipe-based thermal desorber. For example, air from the ambient environment may be directly drawn into the inlet 202, through the chemical analyte 318, and out of the outlet 312 using the pump 314. In some embodiments, the heaters 316 may be resistive heaters, however other configurations may be used in other embodiments. In some cases (e.g., dependent on calibrants and materials of interest), the heaters 316 may be optional.

The analyte detector 318 may include analyte reporters 320, where each analyte reporter 320 is responsive to (e.g., able to detect) a material(s) of interest. The analyte detector 318 also includes illuminators 322 and response detectors 324 associated with the analyte reporters 320. In an embodiment, the analyte detector 318 may be implemented as an MS, an IMS, a fluorescence-based detector, a colorimetric detector, an electrical-based detector, and/or using other technologies, to provide a swipe-based thermal desorber to perform material detection as further discussed herein. For example, an electrical-based detector may be used to detect changes in conductivity of an analyte reporter when the analyte reporter is exposed to a material of interest. Such technologies may be used with one or more heaters or without any heaters.

The power source 326 may be implemented, for example, as a battery to permit mobile and remote use of the detection device 102 (or system 100), a solar power source, a fuel cell, or wall power. In some embodiments, the power source 326 may be a removable battery. The power source 326 may be used to provide power to the various components of the detection device 102 and/or various components of the calibration device 104 (e.g., provided through the electrical interface 204).

The audio component 328 may be implemented, for example, as a speaker or other transducer with corresponding driver circuitry to provide audible sounds to a user of the detection device 102 or system 100. For example, in some embodiments, the audio component 328 may provide audible signals in response to manipulation of the user controls 106 and/or in response to the operations of the processor 302.

In normal operation of the system 100, the audio component 328 may emit an audible signal to indicate that a particular material is present or is not present, when analysis associated with sampling media is complete, that manual user input is required, and/or other audible alerts to indicate a status and/or result of normal operation to the user. In a calibration operation, the audio component 328 may emit an audible signal to indicate that an error occurred during the calibration operation mode, that analysis associated with one or more calibrants is complete, that user input is required, and/or other audible alerts to indicate a status and/or result of the calibration operation to the user.

The communication interface 330 may be implemented as a wired and/or wireless interface connect the detection device 102 (e.g., by Universal, Serial Bus (USB), Ethernet, WiFi, Bluetooth, cellular, infrared, radio, and/or other protocols) with various external devices to update the operating system 306, update the applications 308, and/or communicate data 310. In some embodiments, the communication interface 330 may connect to external power sources (e.g., a power outlet) to charge a battery of the power source 326 and/or to directly power the detection device 102 or system 100. Other components 332 may also be provided as appropriate for various types of the system 100 to support, for example, application specific operations of such devices.

Turning to the calibration device 104, the calibration device 104 also includes a chamber 334, a blocking member 333, a blocking member actuator 335, a heater 336, a heater actuator 338, a fan 339, a calibrant cartridge 340, a calibrant wheel actuator 348, a chamber detector 350 (e.g., also referred to as a sampling media detector, swab detector, swipe detector, or medium detector), an electrical interface 352, a local controller 354, and other components 356. In some cases, the pump 314 may be included in the calibration device 104 rather than the detection device 102. In some cases, the detection device 102 and the calibration device 104 both include pumps.

The chamber 334 provides a volume of space of the calibration device 104 within which to receive a sample for examination. The sample for examination may be sampling media inserted through the slot 110 or one of the calibrant reservoirs 344. In some cases, the heater 336 may heat the sample and/or generally any material disposed in the chamber 334. The chamber 334 may be between the heater 336 and the inlet 202. In an embodiment, for example, the heater 336 may be used to heat the sample for examination to a desired temperature such that the material at least partially vaporizes to provide analytes (e.g., vapor-phase analytes) to the analyte detector 318 via the inlet 202. The heater actuator 338 (e.g., also referred to as a desorber actuator) may be used to position the heater 336 (e.g., via translational and/or rotational motion) to an appropriate position (e.g., predetermined position) to heat the sample. In some cases, the heater 336 may be moved to contact the sample. In an embodiment, the heater 336 may be a resistive heater, however other configurations may be used in other embodiments. The heater actuator 338 may be a direct current (DC) motor, servo actuator, and/or generally any actuator to move the heater 336. The fan 339 may be used to push air through or over the sample to blow at least a portion of the sample from the chamber 334 to the inlet 202.

The blocking member 333 (e.g., also referred to as a blocker) selectively blocks the slot 110 to prevent sampling media, ambient air, and/or generally any material from entering the calibration device 104 during a calibration operation. In this regard, the blocking member 333 may prevent insertion of external media (e.g., sampling media) into the chamber 334 when a calibrant reservoir 344 is in the chamber 334. Any material that enters the calibration device 104 may contaminate or otherwise affect the results from the calibration operation. The blocking member actuator 335 may be used to move the blocking member 333 to block the slot 110 or unblock the slot 110. In some cases, the blocking member 333 may be manually positioned by the user to block or unblock the slot 110.

The calibrant cartridge 340 includes a calibrant wheel 342, one or more calibrant reservoirs 344, and a sealing barrier 346 (e.g., also referred to simply as a barrier). The calibrant wheel 342 may include a structure to hold the calibrant reservoir(s) 344. Each calibrant reservoir 344 may contain (e.g., store) a calibrant. The calibrant(s) may be used to evaluate and/or calibrate the analyte detector 318. For example, a calibrant may be used to elicit a response from at least one analyte reporter 320 of the analyte detector 318 when the analyte reporter 320 is exposed to the calibrant. The sealing barrier 346 may be used to prevent transfer (e.g., leakage) between the analytes associated with the sample for examination (e.g., in the chamber 334) and the calibrant reservoir(s) 344, and vice versa. In this regard, the sample may be a test sample(s) or one of the calibrant reservoirs 344.

The calibrant wheel actuator 348 may be used to position the calibrant wheel 342 (e.g., via translational and/or rotational motion) such that one of the calibrant reservoirs 344 is disposed in the chamber 334. In some cases, the heater actuator 338 may push the heater 336 such that the heater 336 is in contact with the calibrant reservoir 344 in the chamber 334. In some cases, the fan 339 can push air through the calibrant reservoir 344 to provide calibrant of the calibrant reservoir 344 disposed in the chamber 334 as analytes to the analyte detector 318. In this regard, the calibrant wheel 342 may be selectively rotated by the calibrant wheel actuator 348. The calibrant wheel actuator 348 may be a DC motor, servo actuator, and/or generally any actuator to move the calibrant wheel 342.

The calibrant wheel 342 also includes a sealing member 345. The sealing member 345 may be positioned in the chamber 334 and against the inlet 202 to allow checking of leaks downstream of the inlet 202. In this regard, the calibrant wheel actuator 348 can position (e.g., via at least rotational movement) the sealing member 345 in the chamber 334 and push the sealing member 345 against the inlet 202. With the sealing member 345 pushed against the inlet 202, a flow or pressure sensor (e.g., within the detection device 102) may be used to perform pressure measurements associated with the detection device 102 and the processor 302 may be used to check for leaks based at least on the pressure measurements.

The chamber detector 350 may detect whether sampling media and/or any other material is disposed in the chamber 334. For example, the chamber detector 350 may be, may include, or may be a part of, a photo-interrupter diode. In some cases, when the chamber detector 350 detects that sampling media is disposed in the chamber 334, the calibrant wheel actuator 348 may be prevented (e.g., by the chamber detector 350) from rotating the calibrant wheel 342 when the sampling media is detected in the chamber 334.

The electrical interface 352 may couple to the electrical interface 204 of the detection device 102 (e.g., via direct or and/or indirect contact) to receive power and/or control signals from the detection device 102. The power from the detection device 102 may be used to power the various components of the calibration device 104. The local controller 354 may receive control signals from the detection device 102 and provide control signals to the various components of the calibration device 104. In some case, the local controller 354 may be a centralized controller for facilitating operation of the various components of the calibration device 104. Alternatively and/or in addition, the local controller 354 may be distributed between the various components of the calibration device 104.

In some cases, the control signals from the detection device 102 may include high-level instructions, such as an instruction for the calibration device 104 to initiate a calibration operation (e.g., in accordance with predefined parameters). From these high-level instructions, the local controller 354 may autonomously generate control signals to the various components to effectuate the high-level instructions, such as signals to set a temperature of the heater 336, operate the heater actuator 338 and calibrant wheel actuator 348, operate the fan 339, and so forth.

In other cases, alternatively and/or in addition, the control signals from the detection device 102 may define parameters to be used by the various components of the calibration device 104, such as the temperature to set the heater 336. The control signals may be distributed by the local controller 354 and/or provided from the detection device 102 to the calibration device 104 without being received by the local controller 354.

Other components 356 may be provided as appropriate for various types of the calibration device 104 to support, for example, application specific operations of the calibration device 104. The components 356 may include communication capability (e.g., wired, wireless capability), audio and/or video capability, memory, power source(s) (e.g., battery) and/or generally any components that may, but need not, be associated with chemical detection by and/or calibration of the analyte detector 318.

In an embodiment, the calibration device 104 may be operated as a standalone device (e.g., independent of the detection device 102). The calibration device 104 may contain a power source (e.g., battery) and/or connection thereto (e.g., a wired connection to an outlet). For example, in this embodiment, an analyte detector (e.g., provided in paper form) may be placed in the chamber 334 of the calibration device 104. Alternatively, the analyte detector may be placed in proximity to or in contact with a calibrant reservoir 344, such as being pushed by a user against the calibrant reservoir 344, or being pushed against an inlet through which calibrant from the calibrant reservoir 344 may be provided. The fan 339 and/or a pump of the calibration device 104 may be used to blow out a calibrant (e.g., simulant) contained in the calibrant reservoir 344 onto the analyte detector. In some cases, the calibration device 104 may include an inlet through which air from the fan 339 and/or a pump can be received and provided to the calibrant reservoir 344 to blow out a calibrant contained in the calibrant reservoir 344.

When the calibrant contains one or more materials of interest that react to the analyte detector (e.g., provided in paper form), the analyte detector may exhibit a change in electrical properties (e.g., conductivity, resistivity, etc.), a colorimetric response (e.g., change in color), and/or other changes. Such changes may be detected by human inspection, such as a change in color of the analyte detector (e.g., litmus paper), or additional equipment, such as a multimeter to measure electrical properties of the testing sample. In this manner, the calibration operation may be used to test the analyte detector and/or the calibrants contained in the calibrant reservoirs.

Figure 4:
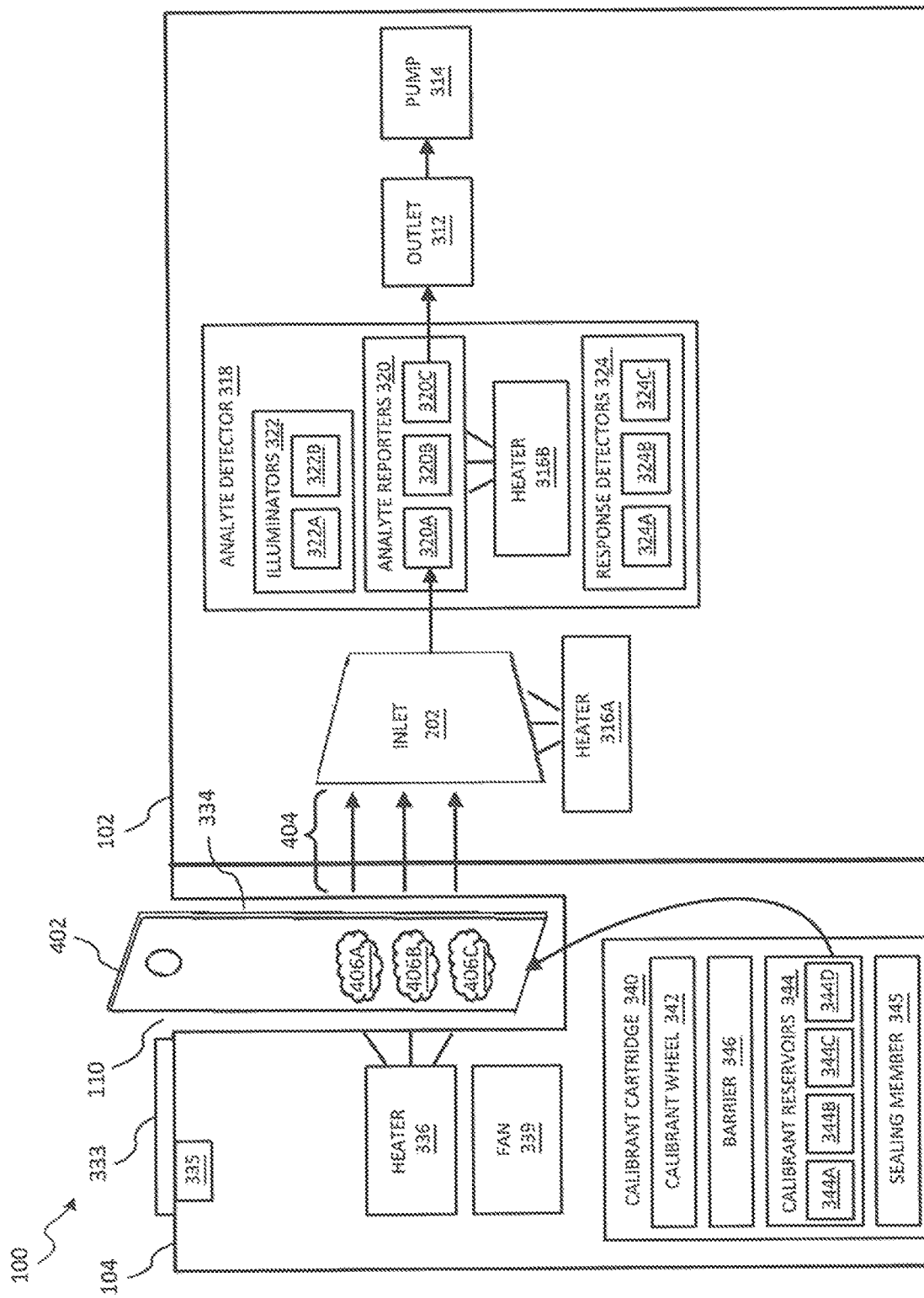
FIG. 4 illustrates an operational flow of analytes through a system in accordance with an embodiment of the disclosure.

FIG. 4 illustrates an operational flow of analytes through the system 100 in accordance with an embodiment of the disclosure. It is noted that not all of the depicted components may be required, however, and one or more embodiments may include additional components not shown in FIG. 4. Variations in the arrangement and type of the components may be made without departing from the spirit or scope of the claims as set forth herein. Additional, fewer, and/or different components may be provided. For example, the pump 314, heaters 316, heater 336, and/or heater actuator 338 may be optional in some embodiments.

As shown, sampling media 402 has been inserted through the slot 110 and is positioned in the chamber 334 of the calibration device 104. The sampling media 402 includes test samples 406A, 406B, 406C, which correspond to three different materials under test that have been picked up by the user's application of the sampling media 402 against one or more surfaces of interest (e.g., surface of a package, luggage, clothing, or other article).

The heater 336 operates to apply heat to the sampling media 402 and test samples 406A-C to raise their temperatures to a desired desorption temperature. For example, the heater 336 may operate to apply the heat in response to control signals provided by the processor 302 of the detection device 102 and/or local controller 354 of the calibration device 104. In some embodiments, the desired desorption temperature may be in the range of approximately 90° C. to approximately 160° C., however higher or lower temperatures may be used as desired (e.g., based on the samples for examination to be at least partially vaporized). In some cases, alternatively or in addition to the heater 336, the heater 316A of the detection device 102 may be used to apply heat to the sampling media 402.

In this regard, the test samples 406A-C may be materials that partially or completely vaporize in response to heat applied by the heaters 336 and/or 316A to provide analytes 404 (e.g., corresponding to vaporized portions of the test samples 406A-C) to the analyte detector 318 via the inlet 202. As an example, the test samples 406A, 406B, and 406C may be 2,4,6-trinitrotoluene (TNT), methamphetamine hydrochloride, and triacetone triperoxide (TATP), respectively, each of which may be detected by the analyte detector 318 (e.g., using one or more analyte reporters 320A-C of the analyte detector 318).

The analyte detector 318 is coupled to the inlet 202 and the outlet 312. The pump 314 may operate to draw at least of a portion of the test samples 406A-C, which includes analytes 404, in and through the inlet 202 of the detection device 102 into the analyte detector 318 and out through the outlet 312. The vaporized materials may exhibit various vapor pressures that facilitate the ability of pump 314 and analyte detector 318 to appropriately receive the analytes 404 (e.g., Research Department explosive (RDX) has a vapor pressure of $5 \times 10^{-7}$ Torr at 20° C., TNT has a vapor pressure of $2 \times 10^{-5}$ Torr at 20° C., glycerol has a vapor pressure of $2.5 \times 10^{-3}$ Torr at 50° C., and ethanol has a vapor pressure of 45 Torr at 20° C.)

The heater 316A may heat the inlet 202, such that the portion of the test sample 406A-C including the analytes 404 are heated by the heater 316A as the portion passes through the inlet 202. In this manner, the heater 316A may maintain the inlet 202 at a temperature sufficient to keep the analytes 404 in the vapor phase. In an embodiment, more specifically, the heater 316A is configured to apply sufficient heat to the inlet 202 to prevent loss of the analytes 404 while the analytes 404 are traveling through the inlet 202 toward the analyte reporters 320A-C.

The analyte detector 318 includes various analyte reporters 320A, 320B, and 320C, illuminators 322A and 322B (e.g., also referred to as excitation sources) associated with analyte reporters 320A and 320B, and response detectors 324A, 324B, and 324C associated with the analyte reporters 320A, 320B, and 320C. Once the analytes 404 are received by the analyte detector 318, the analytes 404 may pass through (e.g., propagate through) and be exposed to the analyte reporters 320A-C. In this regard, the pump 314 pulls the air with the analytes 404 in through the inlet 202, to and through the analyte reporters 320A-C, and out through the outlet 312. By passing through the analyte reporters 320A-C, the analytes 404 are exposed to the analyte reporters 320A-C and thus may interact with (e.g., react to) one or more of the analyte reporters 320A-C. The heater 316B may apply heat to the analyte reporters 320A-C to reduce the formation of "cold spots" where the analytes 404 can lump together. In addition, the heater 316B may help the analytes 404 desorb from the analyte reporters 320A-C to improve subsequent detection of the analytes 404. Based on the response of the analyte reporters 320A-C to the analytes 404, as detected by the response detectors 324A-C, the presence (or lack of presence) of certain materials of interest may be determined.

In some cases, the illuminators 322A and 322B may be used to emit light of a wavelength appropriate to interact with the analytes 404 subsequent to exposure of the analytes 404 to the analyte reporters 320A and 320B, respectively. For example, in response to the excitation from the illuminator 322A, the analyte reporters 320A exposed to the analytes 404 may emit light that is received by the response detector 324A. In this example, the exposure of the analyte reporters 320A and 320B to the analytes 404 may produce a fluorescent response, a change in fluorescence, a luminescent response, and/or a change in luminescence in the analyte reporters 320A and/or 320B. The response detectors 324A and 324B may be configured to (e.g., positioned to)

receive the response associated with the exposure of the analyte reporter 320A and 320B, respectively, to the analytes 404.

In some cases, illuminators are optional with respect to some analyte reporters. For instance, illuminators are not required in chemical detection techniques that do not involve illumination of analyte reporters. For example, when an analyte reporter responds to a material of interest by exhibiting a change in resistivity, illuminators are not needed. In this example, the response of the analyte reporter is exhibited by a corresponding change in current and/or voltage that is detected by an appropriate response detector. With reference to FIG. 4, the analyte reporter 320C does not have an associated illuminator to illuminate the analyte reporter 320C. For example, the analyte reporter 320C may respond to the analytes 404 by exhibiting a change in conductivity. The response detector 324C may be used to determine a current (e.g., change in current), voltage (e.g., change in voltage), and/or other type of signal appropriate to characterize a response of the analytes 404 to the analyte reporter 3200.

Although FIG. 4 illustrates the flow of analytes through the system 100 during normal operation, the flow of analytes also applies to a calibration operation. In this regard, during normal operation, the system 100 (e.g., the analyte detector 318) is used to determine whether materials of interest are present in test samples. During a calibration operation, one or more calibrants (e.g., stored in calibrant reservoirs) are used to evaluate and/or calibrate the system 100, e.g. by testing the response of one or more of the analyte reporters 320A-C to the calibrant(s). In some cases, to facilitate a calibration operation, the blocking member 333 selectively blocks the slot 110 to prevent sampling media, ambient air, and generally any material from entering the calibration device 104 during a calibration operation. The blocking member actuator 335 may be used to move the blocking member 333 to block the slot 110 during a calibration operation, and to unblock the slot 110 after a calibration operation to allow a sample for examination to be received in the chamber 334 via the slot 110.

In some embodiments, the processor 302 of the detection device 102 may generate and provide control signals to various components of the detection device 102 and/or various components of the calibration device 104 to effectuate a calibration operation. In some cases, the control signals may include an instruction to initiate a calibration operation.

A calibration operation may involve testing one or more of the analyte reporters 320A-C. In some cases, the calibration operation may include cycling through some or all of the calibrants in the calibrant reservoirs. The calibration operation may be defined by the user or the processor 302. The calibrant reservoirs that are used in the calibration operation may be based at least on which of the analyte reporters 320A, 320B, and/or 320C is to be evaluated.

In response to the control signals, the calibrant wheel actuator 348 (e.g., shown in FIG. 9) may position the calibrant wheel 342 (e.g., via translational and/or rotational motion) such that one of the calibrant reservoirs 344A-D is disposed in the chamber 334, e.g. between the heater 336 and the inlet 202. The heater actuator 338 may position the heater 336 (e.g., via translational and/or rotational motion) to heat the calibrant reservoir 344 disposed in the chamber 334 to at least partially vaporize the calibrant stored in the calibrant reservoir 344 to provide the vaporized calibrant to the analyte detector 318 via the inlet 202. The vaporized calibrant includes one or more analytes response to one or more analyte reporters of the analyte detector 318. The calibrant reservoir 344 disposed in the chamber 334 may be heated for an amount of time appropriate to desorb and deliver an appropriate amount of calibrant vapor as analytes to the inlet 202. The heater 316A may apply heat to the inlet 202 to maintain the analytes in the vaporized state en route to the analyte detector 318. In some cases, the detection device 102 and calibration device 104 may coordinate such that desorber and inlet temperatures effectuated by the heaters 336 and 316A are appropriate for a specific calibrant. In this regard, different calibrants (e.g., stored in different calibrant reservoirs 344A-D) may be associated with different desorber and/or inlet temperatures.

In some cases, the calibrant cartridge 340 (and/or portion thereof) is a consumable item for the calibration device 104 that can be removed and replaced by the user. For example, the user may replace the calibrant cartridge 340 based on an expiration date of the calibrant cartridge 340, e.g. to ensure that the calibrants themselves are reliable for evaluating and calibrating the analyte detector 318.

The calibration operation may be used to determine responses of the analyte reporters 320A-C to a calibrant contained in one or more of the calibrant reservoirs 344A-D. In some cases, each of the analyte reporters 320A-C is responsive to at least one of the calibrants. The response detectors 324A-C of the analyte detectors 318 may be used to measure a response of the analyte reporters 320A-C to the calibrants and provide response data based on the measured response. The response data may be the measured response or may be derived based on the measured response.

In an embodiment, the response detectors 324A-C provide an intensity of light emitted by the vaporized calibrants upon interaction with the analyte reporters 320A-C. In some cases, for a given calibrant reservoir 344, one or more of the response detectors 324A-C may be used to measure the response of the associated analyte reporters 320A-C to the vaporized calibrant. For example, for the calibrant reservoir 344A, the response of the analyte reporters 320A and 320C to the calibrant stored in the calibrant reservoir 344A may be desired, whereas the response of the analyte reporter 320B to the calibrant is not needed (e.g., the calibrant does not react to the analyte reporter 320B). In one case, the response detector 324B associated with the analyte reporter 320B does not generate any response data and/or the processor 302 does not use any intensity data from the response detector 324B. In another case, the response detector 324B may still be utilized to generate intensity data, since unexpected intensity data from the response detector 324B may be used to determine whether the analyte reporter 320B is properly operating.

For each analyte reporter 320A-C that is tested, the processor 302 (e.g., and/or other processor of the system 100) may determine whether the analyte reporter is operating properly based on responses detected by the corresponding response detector. Such responses may be, or may be used to derive, results of the calibration operation with respect to the analyte reporter.

The processor 302 may perform one or more actions based on whether the analyte reporter is determined to be operating properly. When the results indicate that an analyte reporter is not operating properly and/or is providing inconsistent results, such results may indicate that the analyte reporter may need to be replaced. In this case, the processor 302 (e.g., and/or other processor of the system 100) may automatically or provide an indication to a user (e.g., via the display 108) regarding the error(s) and/or identifying the component(s) (e.g., analyte reporter(s)) of the system 100 that may require maintenance, replacement, and/or further analysis. The user may take corrective action, such as performing additional tests on one or more of the analyte reporter(s) 320A-C and/or removing or replacing the analyte reporter(s) 320A-C determined to not be operating properly. The additional tests may be performed using the system 100 and/or using other systems (e.g., other testing equipment).

In some cases, when an analyte reporter (e.g., 320B) is determined not to operate properly, the analyte reporter may be replaced with another analyte reporter (e.g., of similar or same nominal properties as the analyte reporter 320B being replaced). The replacement analyte reporter may need to be conditioned, such as being placed and left alone in the analyte detector for a certain amount of time (e.g., 5 seconds to 90 seconds for some analyte reporters), before being used. In some cases, after the conditioning (if needed), the replacement analyte reporter (and possibly other analyte reporters) may be tested in a calibration operation.

In an embodiment, alternatively and/or in addition to identifying and indicating errors to the user, in response to the results, the processor 302 (e.g., and/or other processor of the system 100) may selectively calibrate the analyte detector 318 and/or other components of the system 100. In this regard, the processor 302 may determine whether any adjustments (e.g., to the response detectors) are needed and/or are implementable on the analyte detector 318 (e.g., rather than replacement of any analyte reporters). When the analyte reporters 320A-C are determined to operate properly, no calibration is performed (e.g., no adjustments to the analyte detector 318 are made). When one or more of the analyte reporters 320A-C are determined to not be operating properly, the processor 302 may adjust a setting (e.g., a responsivity, sensitivity) of one or more of the response detectors 324A-C corresponding to the analyte reporters 320A-C determined not to be operating properly. As another example, when the response data provided by a response detector is consistently off by a certain amount, the processor 302 may apply an offset to response data received from the response detector, or cause the response detector to apply the offset prior to providing the response data to the processor 302. In some cases, the analyte detector 318 (e.g., some or all of the analyte reporters 320A-C) may be retested in a calibration operation subsequent to the calibration of the analyte detector 318.

In some embodiments, the heaters 316A-B, heater 336, heater actuator 338, and/or fan 339 are optional. For example, alternative and/or in addition to including the heater 336, the fan 339 and/or other fans and/or pumps can be used to push or pull portions of the sample to provide the portions including any analytes therein to the analyte detector 318 via the inlet 202. In this regard, in some cases, the calibrant contained in the calibrant reservoir 344 in the chamber 334 does not need to be heated. In some cases, the pump 314 and/or the fan 339 and/or other fans and/or pumps may be provided in the calibration device 104 and/or the detection device 102. One or more actuators (e.g., in the calibration device 104 and/or detection device 102) to move one or more heaters, one or more fans, and/or one or more pumps as appropriate to provide the analytes from the sample in the chamber 334 to the analyte detector 318.

In an embodiment, the analytes 404 move over each of the analyte reporters 320A-C (e.g., sequentially). In some cases, the analyte reporters 320A-C may be placed in any order. In addition, although illustrated as discrete sections in FIG. 4, the analyte reporters 320A, 320B, and/or 320C may contact each other and/or may be layered over each other in some embodiments.

As an example, the analyte reporter 320A may be operable to detect certain military explosives (and/or explosive-related compounds). For example, such military explosives, explosive-related compounds, and/or components thereof may be contained in a test sample(s) (e.g., one or more of the test samples 406A-C) on the sampling media 402 or contained in a calibrant stored in a calibrant reservoir (e.g., one or more of the calibrant reservoirs 344A-D). In some embodiments, the analyte reporter 320A includes an amplifying fluorescent polymer or other military analyte reporter. The intensity of light emitted by the amplifying fluorescent polymer varies in response to interaction of the amplifying fluorescent polymer with the analytes. For example, the binding of one analyte molecule to the amplifying fluorescent polymer quenches the emission of many polymer repeat units. Thus, when an analyte of interest lands on a polymer binding site, many polymer repeat units in the vicinity of the bound analyte do not emit absorbed light as fluorescence. As a result, the polymer fluorescence is said to be "quenched" by the adsorption of the analyte molecule.

In various embodiments, the analyte reporter 320A is associated with the illuminator 322A having an associated wavelength and the response detector 324A (e.g., an optical detector). The illuminator 322A (e.g., an LED) emits light of a wavelength appropriate to interact with the amplifying fluorescent polymer to cause the amplifying fluorescent polymer to generate an emission. As an example, the wavelength may be about 400 nm (e.g., 365 nm). The response detector 424A (e.g., a photodiode) is positioned to receive the emission generated by the amplifying fluorescent polymer to detect the presence of one or more analytes. The illuminator 322A and the response detector 324A may be positioned such that light emitted by the illuminator 322A is not captured by the response detector 324A (e.g., the response detector 324A captures mostly the emission generated by the amplifying fluorescent polymer). Other dispositions of illuminator 322A and response detector 324A are contemplated, and illuminator 322A and response detector 324A can be positioned in any desired configuration (e.g., in proximity or co-located in some embodiments).

Examples of analytes that are detectable by the analyte reporter 320A include TNT (e.g., test sample 406A). Other substances that may be detected are disclosed in U.S. Pat. No. 6,558,626, which is incorporated by reference in its entirety by express reference thereto.

In an example, the analyte reporter 320B may be operable to detect certain amine-based substances, such as amine compounds like methamphetamine hydrochloride (e.g., test sample 406B). The analyte reporter 320B includes protonated 2-[5-methoxy-2-(4-phenyl-quinoline-2yl)-phenyl]-ethanol (PQP), which is fluorescent. For example, such amine-based substances and/or components thereof may be contained in a test sample(s) on the sampling media 402 or contained in a calibrant stored in a calibrant reservoir. Changes in the fluorescence (i.e., increases or decreases in the response of the protonated PQP of the analyte reporter 320B to light) establish the presence of an amine compound. For example, upon reaction of an amine compound with the protonated PQP of the analyte reporter 320B, the protonated PQP may undergo a change in fluorescent response intensity. In some embodiments, the amine compound deprotonates the protonated PQP of the analyte reporter 320B to produce a decreased fluorescent response. In this regard, the response of the protonated PQP may exhibit a decrease in fluorescence intensity as time progresses due to the deprotonation by the amine compound of the protonated PQP in the analyte reporter 320B.

The analyte reporter 320B is associated with the illuminator 322B having an associated wavelength (e.g., 365 nm or 405 nm) and the response detector 324B (e.g., an optical detector). The illuminator 322B (e.g., a LED) emits light in a wavelength that interacts with the protonated PQP of the analyte reporter 320B to cause the protonated PQP to generate an emission. The response detector 324B is positioned to receive the emission generated by the protonated PQP of the analyte reporter 320B to detect the presence of an amine compound. The response detector 324B detects the changes in response of the protonated PQP of the analyte reporter 320B to thereby establish the presence of an amine compound. The illuminator 322B and the response detector 324B may be positioned such that light emitted by the illuminator 322B is not captured by the response detector 324B (e.g., the response detector 324B captures mostly the emission generated by the amplifying fluorescent polymer).

In an example, the analyte reporter 320C may be operable to detect certain peroxide-based explosives, such as peroxide-containing compounds like hydrogen peroxide and urea hydrogen peroxide, and peroxide precursors like TATP (e.g., test sample 406C). For example, such peroxide-based explosives and/or components thereof may be contained in a test sample(s) (e.g., one or more of the test samples 406A-C) on the sampling media 402 or contained in a calibrant stored in a calibrant reservoir (e.g., one or more of the calibrant reservoirs 344A-D). In some embodiments, the analyte reporter 320C includes a light-emitting peroxide-reactive compound and is associated with the response detector 324C (e.g., an optical detector). Light-emitting materials suitable for use may be any luminescent material, including dyes, oligomers, polymers, and combinations thereof. The light-emitting material may be selected to exhibit certain properties, such as a particular emission wavelength, high quantum yield, high output light efficiency when formulated in a peroxide reactive system, and/or compatibility (e.g., solubility) with one or more components of the system. Additional details regarding the light-emitting materials are found in U.S. Pat. No. 9,005,524, which is incorporated by reference in its entirety by express reference thereto.

The light-emitting peroxide-reactive material responds to the hydrogen peroxide generated from peroxide-containing compounds or peroxide precursors to produce energy in the form of the emission of a photon. In some embodiments, the resulting energy can stimulate luminescence of the light-emitting peroxide-reactive material such that light energy is emitted. The resulting emission may be detected by the response detector 324C, which signals the presence of hydrogen peroxide (and a peroxide precursor and/or a peroxide-containing compound).

In some embodiments, a calibration operation performed using a single calibrant may, in some embodiments, be used to calibrate more than one analyte reporter. In this regard, two or more of the analyte reporters 320A-C may be responsive to the same or similar types of compounds. For example, the analyte reporters 320A and 320B (and/or analyte reporters 320A and 320C) may each include protonated PQP to detect the presence of amine compounds. In this way, an amine calibrant can interact with and be detected at more than one analyte reporter for calibration purposes.

It is noted that FIG. 4 (and other figures) illustrate example numbers and arrangements of heaters 316 and 336, calibrant reservoirs 344, illuminators 322, analyte reporters 320, response detectors 324, and other components. For example, although the analyte detector 318 includes three analyte reporters 320A-C in FIG. 4, more or fewer analyte reporters may be included in the analyte detector 318. In other embodiments, the system 100 may include more or fewer of these components, and/or different components and/or arrangements thereof.

Figure 5:
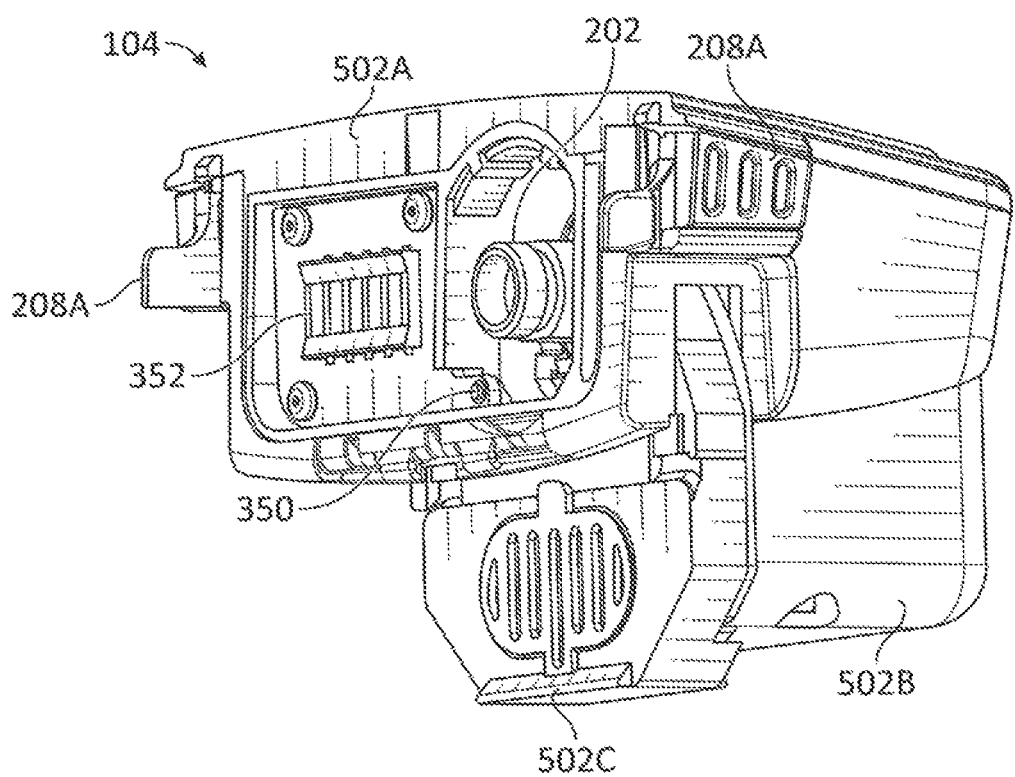
FIGS. 5 and 6 illustrate perspective views of a calibration device in accordance with embodiments of the present disclosure.
Figure 6:
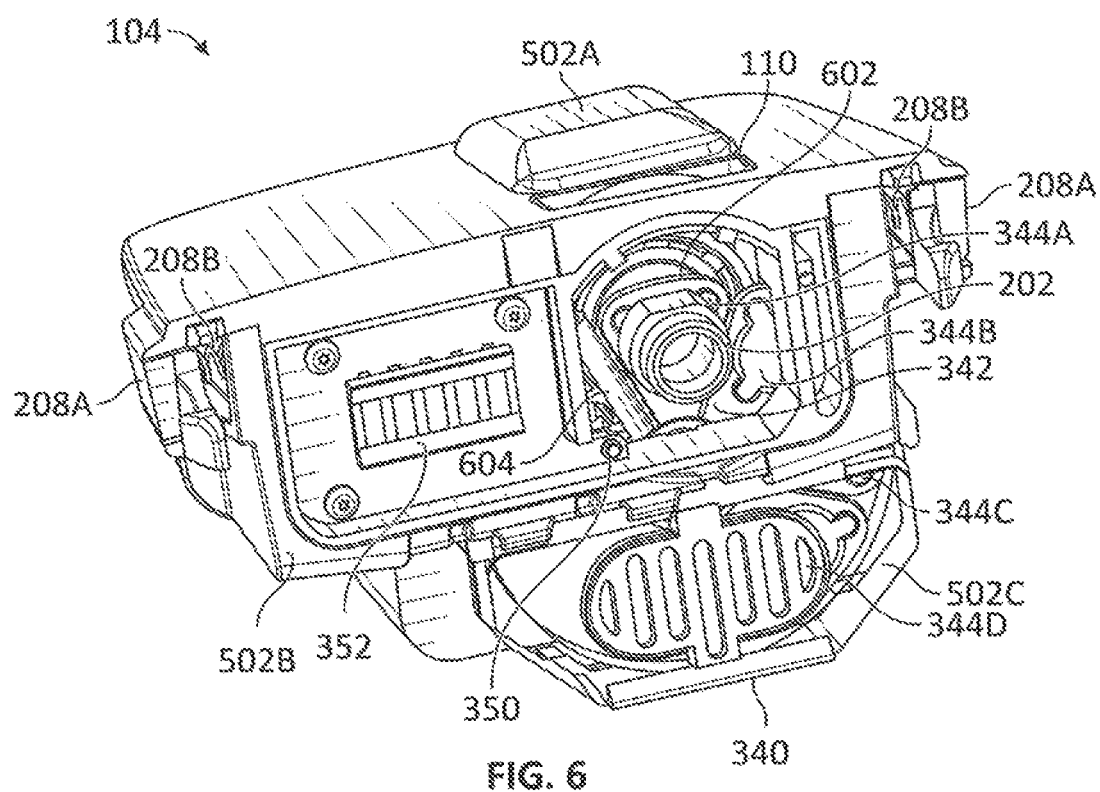
Figure 7:
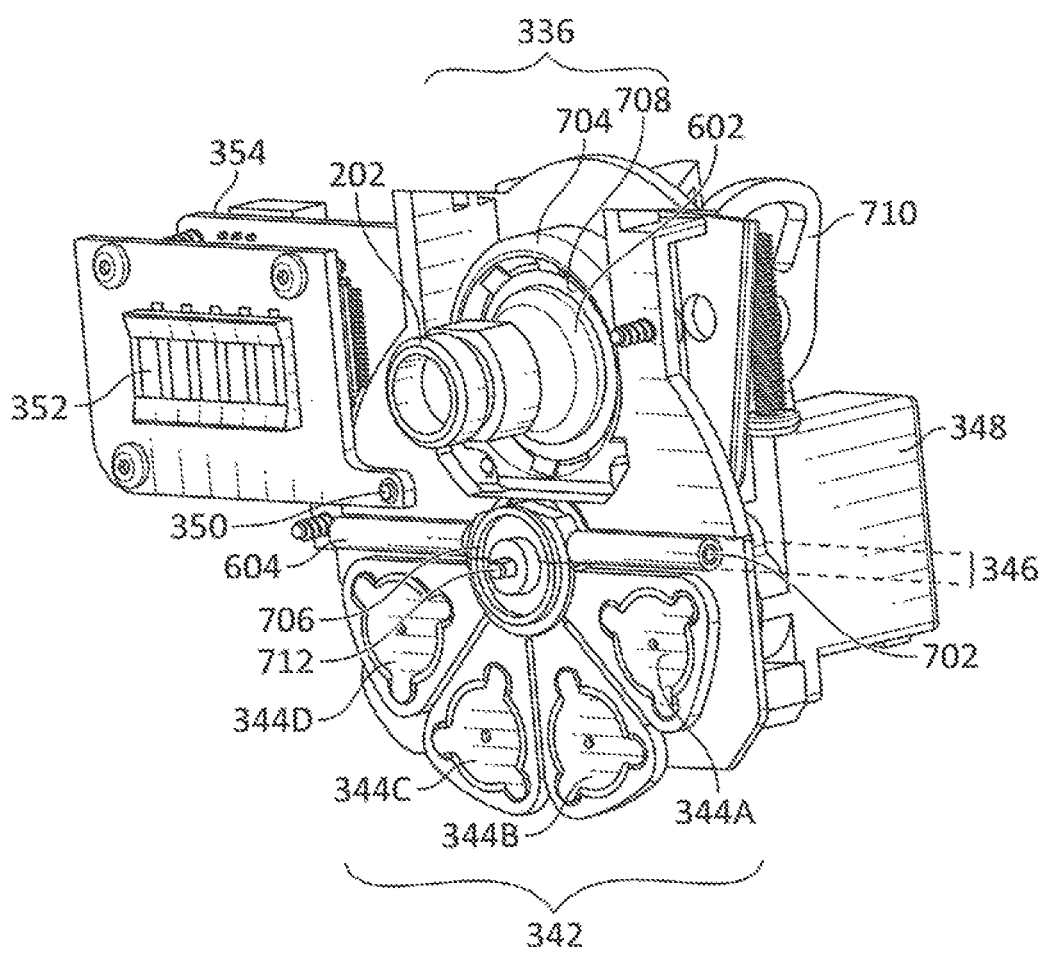
FIGS. 7 through 9 illustrate perspective views of a calibration device with various covers removed in accordance with embodiments of the present disclosure.
Figure 8:
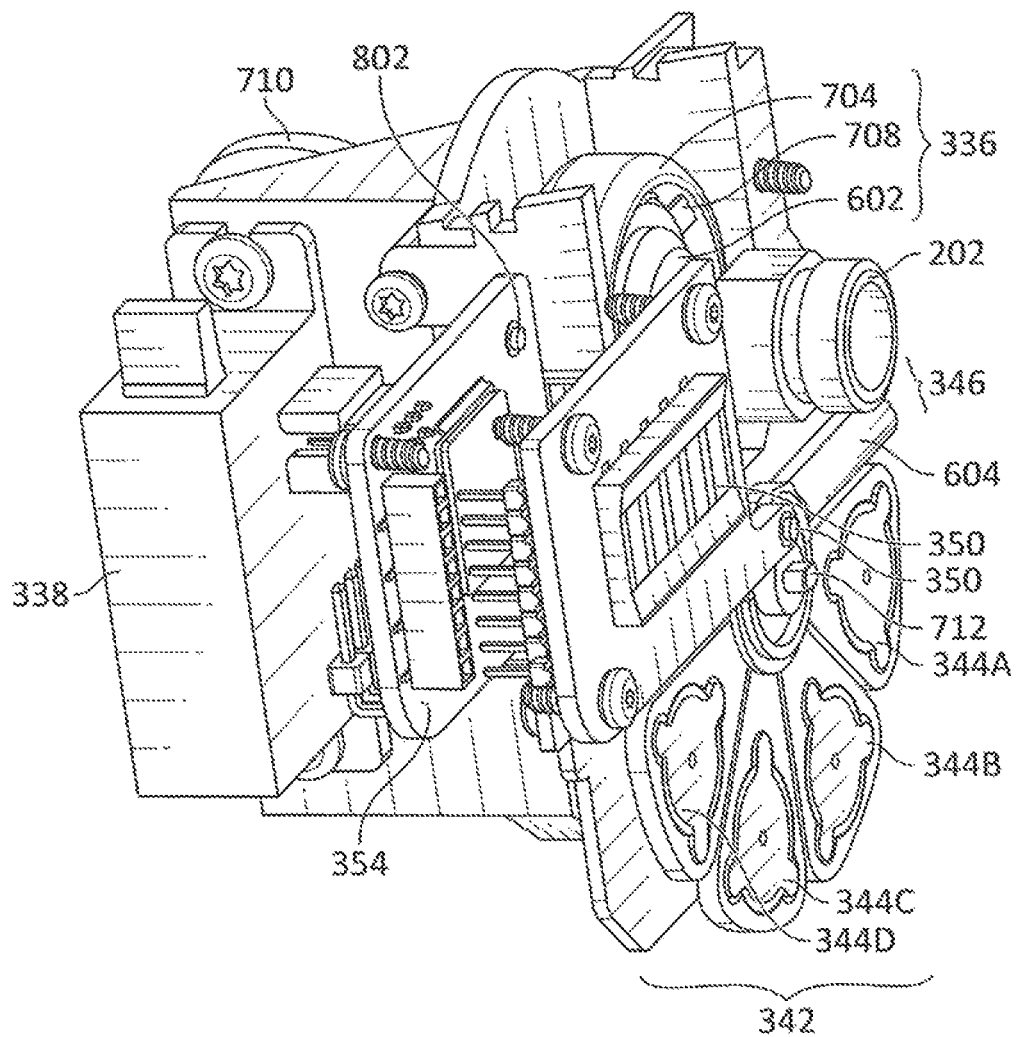
Figure 9:
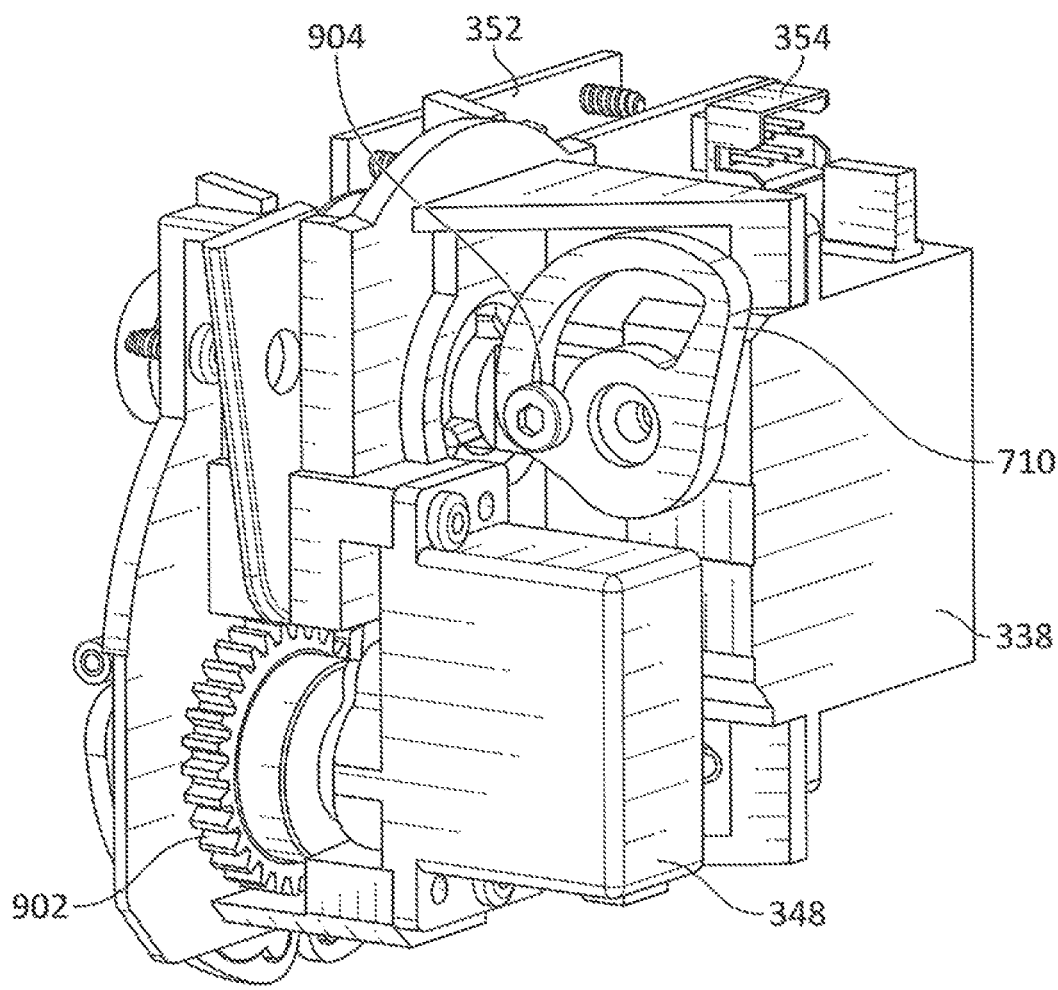

FIGS. 5 and 6 illustrate perspective views of the calibration device 104 in accordance with embodiments of the present disclosure. FIGS. 7 through 9 illustrate perspective views of the calibration device 104 with various covers 502A-C removed in accordance with embodiments of the present disclosure. It is noted that not all of the depicted components may be required, however, and one or more embodiments may include additional components not shown in FIGS. 5 through 9. Variations in the arrangement and type of the components may be made without departing from the spirit or scope of the claims as set forth herein. Additional, fewer, and/or different components may be provided. For example, the heater 336 and heater actuator 338 of may be optional in some embodiments. Although the inlet 202 is described as being part of the detection device 102 and not part of the calibration device 104, the calibration device 104 may include the inlet 202 and/or another inlet.

The calibration device 104 includes covers 502A-C. For example, the covers 502A and 502B may be, or may be referred to as, a top cover and a side cover, respectively. The cover 502C may be used to cover the calibrant cartridge 340 (e.g., and/or components thereof). The covers 502A-C may be releasably attached to different components of the calibration device 104. For example, one or more of the covers 502A-C may be removed to facilitate access to various components enclosed by the covers 502A-C, such as to clean components, replace components, tighten components (e.g., tighten screws), and/or clean the covers 502A-C. As shown in FIGS. 5 and 6, the spring-loaded tabs 208 may be implemented as tabs 208A with associated springs 208B to facilitate attaching the calibration device 104 to and detaching the calibration device 104 from the detection device 102.

The slot 110 may be defined in the cover 502A. In some cases, the calibration device 104 may include a blocking member 333 to selectively block the slot 110 to prevent sampling media, ambient air, and generally any material from entering the calibration device 104 (e.g., at least during a calibration operation).

The heater 336 may be implemented as a heated plate 602 maintained in a sled 704 (e.g., movable sled) by a washer ring 708. The heater actuator 338 may be used move the heater 336 (e.g., via translational and/or rotational motion) in proximity to or in contact with a sample for examination (e.g., sampling media containing test samples, calibrant reservoir containing calibrant) in the chamber of the calibration device 104 in order to heat the sample, which may include analytes, to provide at least a portion of vaporized sample to the inlet 202. In an embodiment, the heater actuator 338 may move the heated plate 602 such that the heated plate 602 is in contact with the sample for examination (e.g., sampling media in normal operation, calibrant reservoir in a calibration operation). For example, the heater actuator 338 may move the heater 336 in response to control signals provided by the detection device 102 to the calibration device 104 (e.g., via the electrical interface 204) and/or the local controller 354.

In FIG. 6, the cartridge cover 502C is shown transparently to illustrate components of the calibrant cartridge 340. The calibrant cartridge 340 includes the calibrant wheel 342, the calibrant reservoirs 344A-D, the sealing barrier 346, a hub 706. In operation (e.g., during a calibration operation), the calibrant wheel actuator 348 may move the calibrant wheel 342 to position one of the calibrant reservoirs 344A-D in the chamber. For example, the calibrant wheel actuator 348 may move the calibrant wheel 342 in response to control signals provided by the detection device 102 to the calibration device 104 and/or the local controller 354.

In FIG. 6, the calibrant wheel actuator 348 has rotated the calibrant wheel 342 such that the calibrant reservoir 344A is disposed in the chamber and positioned between the inlet 202 and the heated plate 602. In some cases, the chamber detector 350 (e.g., a photo-interrupter diode) may be used to detect whether sampling media and/or any other material is disposed in the chamber 334. The chamber detector 350, calibrant wheel actuator 348, processor 302, and/or other component of the system 100 may prevent rotation of the calibrant wheel 342 when the sampling media is detected in the chamber and may allow rotation of the calibrant wheel 342 when the sampling media is removed from the chamber.

The sealing barrier 346 includes a longitudinal bar 702 having a tubing 604 disposed thereon. The hub 706 receives the longitudinal bar 702. In an embodiment, during normal operation, the sealing barrier 346 may be used to prevent transfer of test samples (e.g., 406A-C) and/or associated analytes (e.g., 404) to calibrants of the calibrant reservoirs 344, and vice versa. In other words, the sealing barrier 346 may be used to prevent contamination of test samples and/or associated analytes by calibrants, and prevent contamination of calibrants by test samples and/or associated analytes.

One or more calibrant reservoir position sensors 802 may be used to determine whether a calibrant reservoir is positioned correctly in the chamber. For example, a calibrant reservoir may be determined to be positioned correctly when the calibrant reservoir is at a position in the chamber and between the inlet 202 and heater 336 as appropriate to be heated by the heater 336 and provide analytes to the inlet 202. In some cases, the calibrant reservoir position sensor(s) 802 may be used to determine which of the calibrant reservoirs 344A-D is positioned in the chamber. In some cases, each calibrant reservoir 344A-D may include a barcode that identifies the calibrant reservoir (and/or calibrant contained therein) that can be scanned by the calibrant reservoir position sensor(s) 802. For example, the calibrant reservoir position sensor(s) 802 may be able to properly scan the barcode when the calibrant reservoir is positioned correctly and/or may determine the position of the calibrant reservoir based on the position of the barcode.

In some cases, the calibrant reservoir position sensor(s) 802 may identify the calibrant reservoir (and/or calibrant contained therein) based on a position of the calibrant reservoir in the calibrant wheel 342 relative to the other calibrant reservoirs. Such information may be stored in the memory 304 and/or provided by the processor 302. In FIG. 8, the calibrant reservoir position sensor 802 is located on the local controller 354. In other embodiments, a calibrant reservoir position sensor(s) may be a discrete component and/or may be implemented as part of another component.

Figure 10:
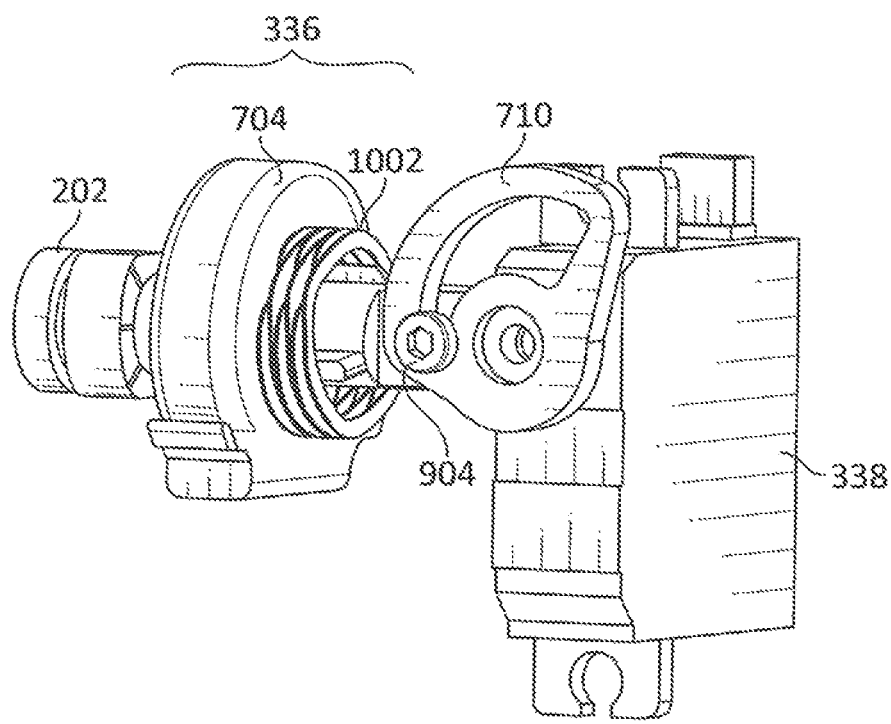
FIG. 10 illustrates a heater and associated components in accordance with an embodiment of the present disclosure.

FIG. 10 illustrates the heater 336 and associated components in accordance with an embodiment of the present disclosure. In FIG. 10, the various components are in a resting configuration. In this resting configuration, a spring 1002 applies tension on the sled 704 of the heater 336 suitable to push the sled 704 toward the inlet 202. A pin 904 holds the sled 704 in position, such that the tension applied by the spring 1002 is not sufficient to push the sled 704 toward the inlet 202.

The heater actuator 338 causes the various components to transition out of the resting configuration, such as in response to control signals to heat a sample for examination (e.g., test sample, calibrant reservoir). The heater actuator 338 generates a torque to cause the cam 710 to rotate (e.g., counterclockwise in FIG. 10). The pin 904 moves in the direction of the inlet 202 in response to the rotation of the cam 710. The movement of the pin 904 causes (e.g., allows) the tension exerted by the spring 1002 on the sled 704 to be exerted on the sled 704 and move the sled 704 toward the inlet 202. As previously indicated, the heater 336 may be implemented as the heated plate 602 maintained in the sled 704 by the washer ring 708. Thus, the heater actuator 338 moves the sled 704 together with the heated plate 602 and washer ring 708 toward the inlet 202 to allow the heated plate 602 to be positioned to heat the sample for examination in the chamber. In some cases, the heater 336 (e.g., the heated plate 602) is moved by the heater actuator 338 such that the heater 336 is in contact with or in proximity to sampling media (e.g., 402) or a calibrant reservoir. In some embodiments, the heater 336 and heater actuator 338 are optional.

Figure 11:
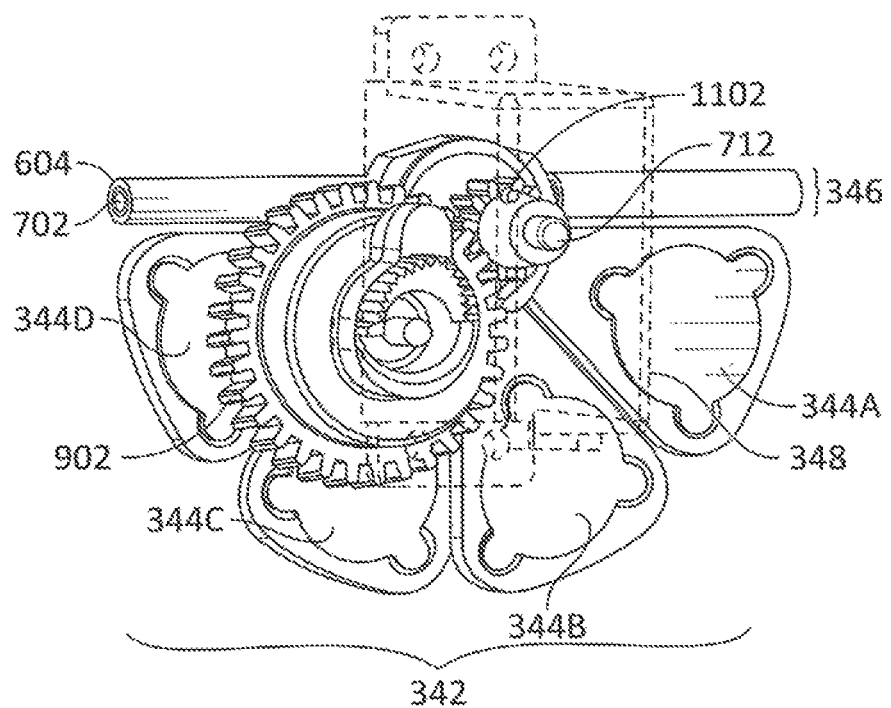
FIG. 11 illustrates a calibrant wheel and associated components in accordance with an embodiment of the present disclosure.

FIG. 11 illustrates the calibrant wheel 342 and associated components in accordance with an embodiment of the present disclosure. The calibrant wheel actuator 348 may generate a torque that causes a gear 902 to rotate. The rotation of the gear 902 in turn causes a gear 1102 (e.g., a smaller gear) to rotate. In this regard, the gears 902 and 1102 may form two meshing gears. The rotation of the gear 1102 causes a spindle 712 to rotate. The rotation of the spindle 712 causes the calibrant cartridge 340 (e.g., the sealing barrier 346 and calibrant wheel 342) to rotate. The calibrant cartridge 340 may be rotated by the calibrant wheel actuator 348 to selectively position (and maintain in position) one of the calibrant reservoirs 344A-D between the heater 336 and the inlet 202 while also positioned in the chamber to facilitate a calibration operation. As one or more of the calibrant reservoirs 344A-D are cycled through during a calibration operation, the calibrant wheel 342 may be rotated by the calibrant wheel actuator 348 to move one of the calibrant reservoirs 344A-D out of the chamber and another of the calibrant reservoirs 344A-D in the chamber.

Figure 12:
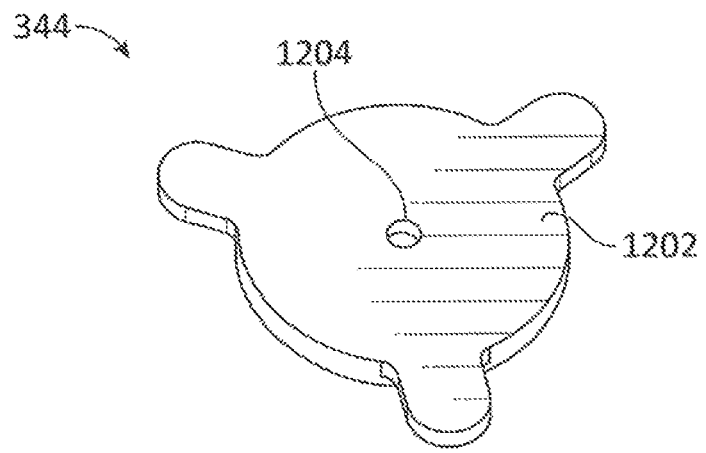
FIG. 12 illustrates a calibrant reservoir lid with a vent in accordance with an embodiment of the present disclosure.

FIG. 12 illustrates a calibrant reservoir lid 1202 with a vent 1204 of a calibrant reservoir 344 in accordance with an embodiment of the present disclosure. For example, the calibrant reservoir 344 may be one of calibrant reservoirs 344A-D or any other calibrant reservoir. The lid 1202 includes a vent 1204 (e.g., also referred to as an exhaust hole) that may be used to pass vaporized calibrant, e.g. to an analyte detector (e.g., 318) via an inlet (e.g., 202). The vent 1204 is implemented as a circular aperture defined in the lid 1202. The center hole diameter may be sized to regulate an amount of analyte provided to the analyte detector 318. The vent 1204 may be implemented using other shapes and sizes as appropriate to pass vaporized calibrant in other embodiments. In some cases, the lid 1202 attaches to a base of the calibrant reservoir 344 and encloses the calibrant except for the vent 1204. In some cases, the calibrant reservoir may be implemented with vent holes on the sides to increase air flow.

Figure 13:
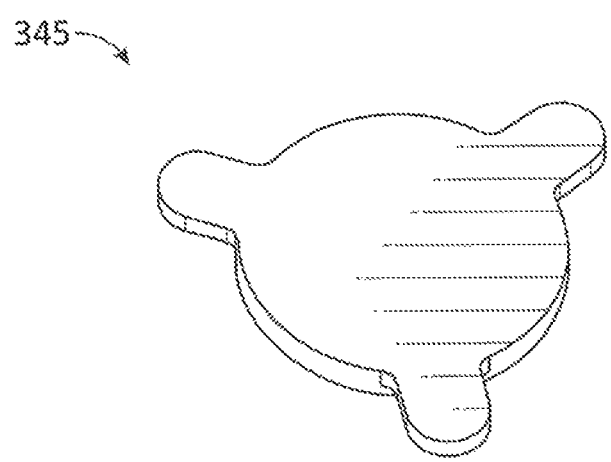
FIG. 13 illustrates a sealing member in accordance with an embodiment of the present disclosure.

FIG. 13 illustrates a sealing member 345 in accordance with an embodiment of the present disclosure. The sealing member 345 may be provided in a calibrant wheel (e.g., 342). In some cases, the sealing member 345 may be shaped and sized similarly to a calibrant reservoir 344. In these cases, the sealing member 345 can be considered a calibrant reservoir that contains no calibration and has no vents. In other cases, the sealing member 345 may be shaped and/or sized differently from a calibrant reservoir 344, and the calibrant wheel may have structure to accommodate (e.g., structure dedicated for) the sealing member 345. In some cases, a surface of the sealing member 345 may be pushed against an inlet (e.g., 202) associated with an analyte detector (e.g., 318), and a flow or pressure sensor (e.g., within the analyte detector) may be used to check for leaks. In this regard, the sealing member 345 may be positioned in the chamber (e.g., 334) of the calibration device (e.g., 104) to check for leaks downstream of the inlet (e.g., leaks in an analyte detector or route therebetween).

Figure 14A:
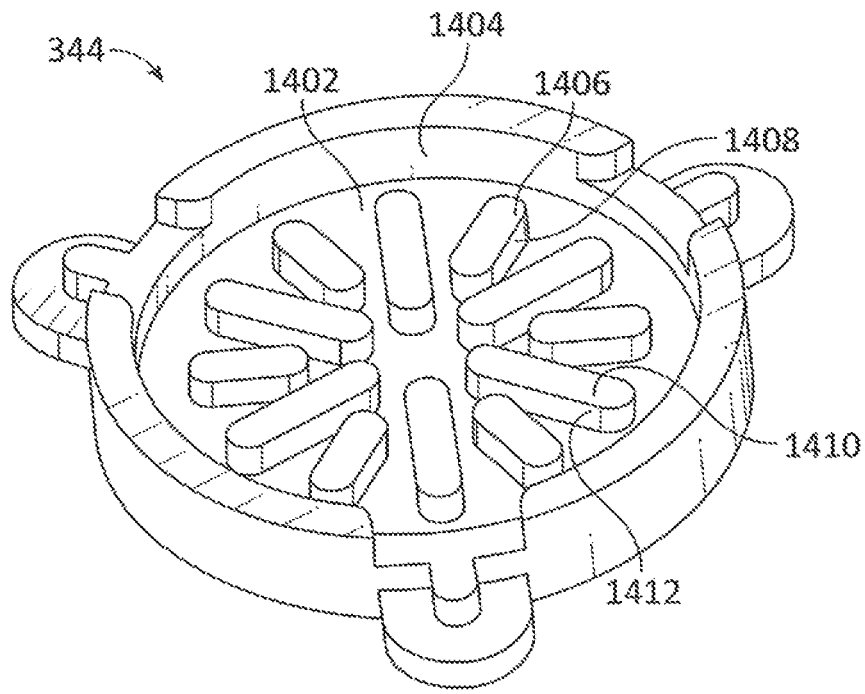
FIG. 14A illustrates a calibrant reservoir base with protrusions in accordance with an embodiment of the present disclosure.
Figure 14B:
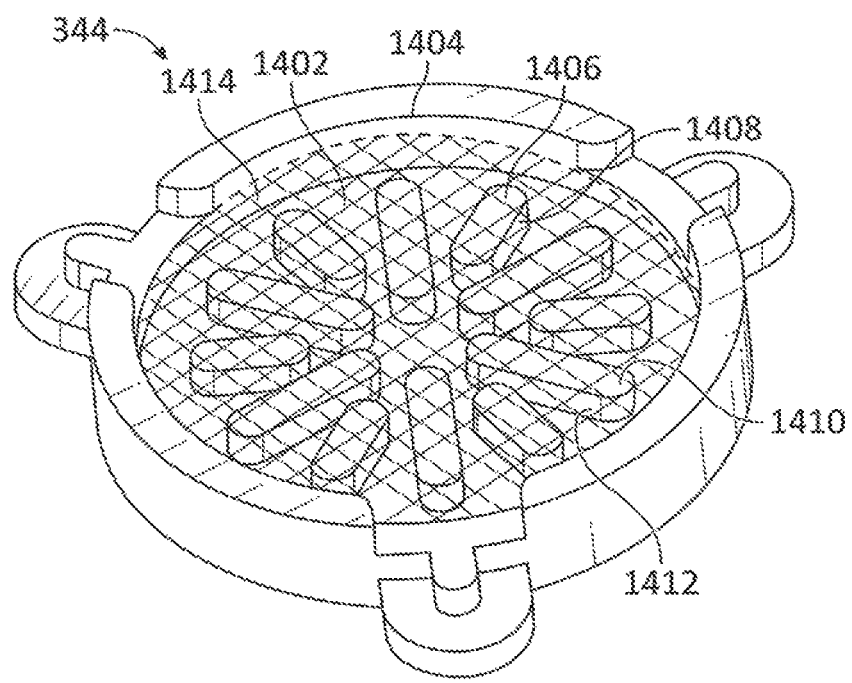
FIG. 14B illustrates a calibrant reservoir base with mesh features in accordance with an embodiment of the present disclosure.

FIG. 14A illustrates a calibrant reservoir base 1402 with protrusions in accordance with an embodiment of the present disclosure. FIG. 14B illustrates a calibrant reservoir base 1402 with a mesh 1414 in accordance with an embodiment of the present disclosure. In some cases, the calibrant reservoir base 1402 may be used in the calibrant reservoir 344 shown in FIG. 12. A surface of the base 1402 includes side walls 1404 and other protrusions having top surfaces (e.g., 1406, 1410) and side surfaces (e.g., 1408, 1412) disposed thereon. The base 1402, side walls 1404, and lid 1202 define a volume for storing the calibrant. The protrusions increase an interior surface area of the calibrant reservoir 344 for receiving (e.g., storing) the calibrant. In this regard, the various surfaces (e.g., 1406, 1408, 1410, 1412) of the protrusions provide surface area onto which the calibrant may adhere. The base 1402 (e.g., including side walls 1404 and protrusions) and lid 1302 define a volume of the calibrant reservoir 344 that can be used to store a calibrant. In FIG. 14B, the base 1402 also includes the mesh 1414. The mesh 1414 may be a gas-permeable membrane through which vaporized calibrant (e.g., vaporized solid, gel, and/or liquid calibrant) can pass. The mesh 1414 may maintain the calibrant in solid form within the volume of the calibrant reservoir for storing the calibrant, and pass the calibrant in vaporized form to the vent 1204. It is noted that the protrusions shown in FIGS. 14A and 14B are optional in some embodiments.

In an embodiment, the calibrant reservoir 344 may be implemented using a material with high thermal conductivity, such as aluminum, aluminum alloy, nickel alloy, and/or other thermally conductive material. In this regard, thermal mass, thermal conductivity, and geometry of the calibrant reservoir 344 are factors that affect a rate of release of the calibrant. In another embodiment, the calibrant reservoir 344 may be implemented using a non-thermally conductive material, such as plastics. For example, non-thermally conductive material may be selected based on cost and/or volatility of calibrants. Materials such as stamped metal or other suitable metal may be used for the calibrant reservoir 344. In some cases, the calibrant reservoir 344 and/or components thereof may be manufactured using a selective laser sintering (SLS) process. In these cases, an EOS aluminum ($AlSi_{10}Mg$) may be used. In some cases, cast aluminum or cast aluminum alloy may be used. Other examples of calibrant reservoir materials may include, by way of non-limiting example, fluorinated ethylene propylene (FEP), perfluoroalkoxy (PFA), polyvinylidene difluoride (PVDF), and nylon (e.g., nylon 6). Different reservoir materials may be utilized for different calibrants, as would be understood by one skilled in the art.

In an aspect, a passivation coating is optionally provided for the calibrant reservoir 344. In some cases, the passivation coating may improve a response and/or lifetime associated with the calibrant reservoir 344 and/or the calibrant contained therein. In one example, a Silcotek Dursan® coating may be provided for an aluminum reservoir having a cupric nitrate calibrant contained therein. In this example, the coating may improve a response and lifetime of the cupric nitrate calibrant. As such, in various aspects, different reservoir materials may be utilized for different calibrants, where different reservoir coatings may optionally be provided based on the reservoir material utilized and/or the calibrant contained therein.

Calibrants contained in the various calibrant reservoirs 344 are generally selected based on an application of the detection system (e.g., materials of interest of the detection system). In this regard, the calibrants provided in the calibrant reservoirs may be determined by the analyte reporters used in the analyte detector. By way of non-limiting examples, the calibrants may include common or specialized explosives (nitroamines, RDX, pentaerythritol tetranitrate (PETN), etc.) or their simulants (like those found in Jehuda Yinon's "Advances in Analysis and Detection of Explosives," *Proceedings of the 4th International Symposium on Analysis and Detection of Explosives*, Sep. 7-10, 1992), chemical and biological warfare simulants (Dimethyl methylphosphonate (DMMP), etc.), and narcotics (heroin, methamphetamines, cocaine, psychoactive drugs, etc.). Other calibrants may be used in other embodiments.

In some cases, the calibrant reservoir 344 may be coated with an inert or corrosion resistant coating to prevent chemical interactions between the calibrant and the material of the base 1302. Some calibrants may be dosed into the base 1302 from a solvent solution and left there until the solvent evaporates. In some embodiments, a calibrant may be provided in the calibrant reservoir 344 in solid form, gel form, or liquid form. For example, the calibrant reservoir 344 may include a gas permeable membrane over a calibrant (e.g., solid, gel, liquid), in which at least partially vaporized calibrant (e.g., obtained from heating the calibrant) can pass. In some cases, the calibrant reservoirs 344 may include a flushing agent (e.g., acetone, toluene, water, mixture thereof) to flush out or revitalize the detection device and/or calibrant reservoirs 344.

Figure 15:
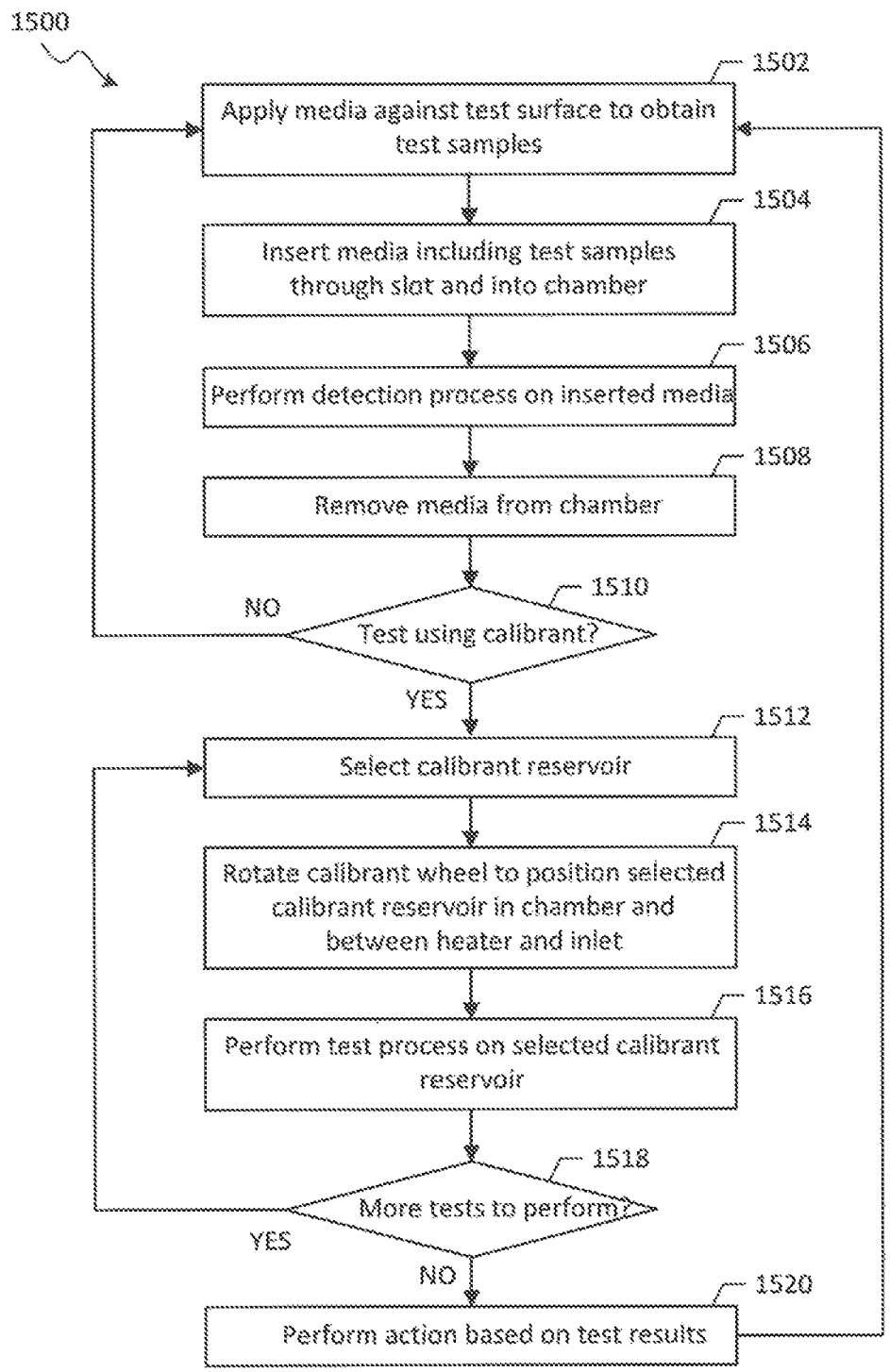
FIG. 15 illustrates a process of operating a system to perform calibration in accordance with an embodiment of the disclosure.

FIG. 15 illustrates a process 1500 of operating the system 100 to perform calibration in accordance with an embodiment of the disclosure. At block 1502, a user applies the sampling media 402 against a test surface (e.g., a package, luggage, clothing, or other article) to obtain one or more test samples (e.g., test samples 406A-C as shown in FIG. 4) corresponding to trace materials residing on the test surfaces.

At block 1504, the user inserts the sampling media 402 through the slot 110 and into the chamber 334 as shown in FIG. 3. At block 1506, a detection process is performed on the inserted sampling media 402. An example process for performing the detection process is described with respect to FIG. 15. At block 1508, the sampling media 402 is removed from the chamber 334.

In an embodiment, use of the sampling media 402 may not be necessary, as the inlet 202 may be used to directly sample ambient air for analytes (e.g., vapor-phase analytes). Additional devices (e.g., coupled to or part of the calibration device 104 and/or detection device 102) may be used to direct the sampled ambient air, which may include analytes, into the inlet 202, such as an air filter/concentrator positioned in the flow path of the sampled ambient air.

At block 1510, a determination is made as to whether to test a calibrant. In an embodiment, one or more calibrants may be tested as part of a calibration operation. The calibration operation may be initiated by the user of the system 100 or autonomously by the processor 302.

When the determination is test a calibrant, a calibrant reservoir (e.g., one of the calibrant reservoirs 344A-D) is selected at block 1512. The calibrant reservoir may be selected based on the control signals from the processor 302.

For example, the control signals may identify which of the calibrant reservoirs to test during the calibration operation and/or in what order to test the calibrant reservoirs. In some cases, the calibration device 104 (e.g., the local controller 354) may have autonomy to determine the order to test the calibrant reservoirs.

At block 1514, the calibrant wheel actuator 348 causes the calibrant wheel 342 to rotate such that the selected calibrant reservoir is positioned between the heater 336 and the inlet 202 while also positioned in the chamber 334. In some cases, the heater 336 (e.g., the heated plate 602) may be moved in contact with the selected calibrant reservoir. At block 1516, a calibrant testing process is performed on the selected calibrant reservoir. An example process for performing the calibrant testing process is described with respect to FIG. 16.

At block 1518, a determination is made as to whether there are additional calibrants to use for testing. The process proceeds to block 1512 when there are additional calibrants to use for testing. When there are no additional calibrants to use for testing, the processor 302 performs an action(s) based on test results at block 1520. For example, when the test results indicate that all the analyte reporters tested by the calibrants are working properly, no action needs to be performed in response to the testing results. As another example, when one or more analyte reporters are determined not to operate properly, the processor 302 may provide for display (e.g., on the display 108) an indication to a user the analyte reporter(s) that are not operating properly, analyte reporter(s) that are operating properly, suggested action(s) (e.g., replace faulty analyte reporter(s), perform further analysis, etc.), and/or other information. The user may take corrective action, such as performing additional tests on analyte reporter(s) and/or removing or replacing analyte reporter(s) determined to not be operating properly. As another example, in some cases, the processor 302 may adjust the response detector associated with an analyte reporter based on the test results, such as adjusting a responsivity of the response detector.

Figure 16:
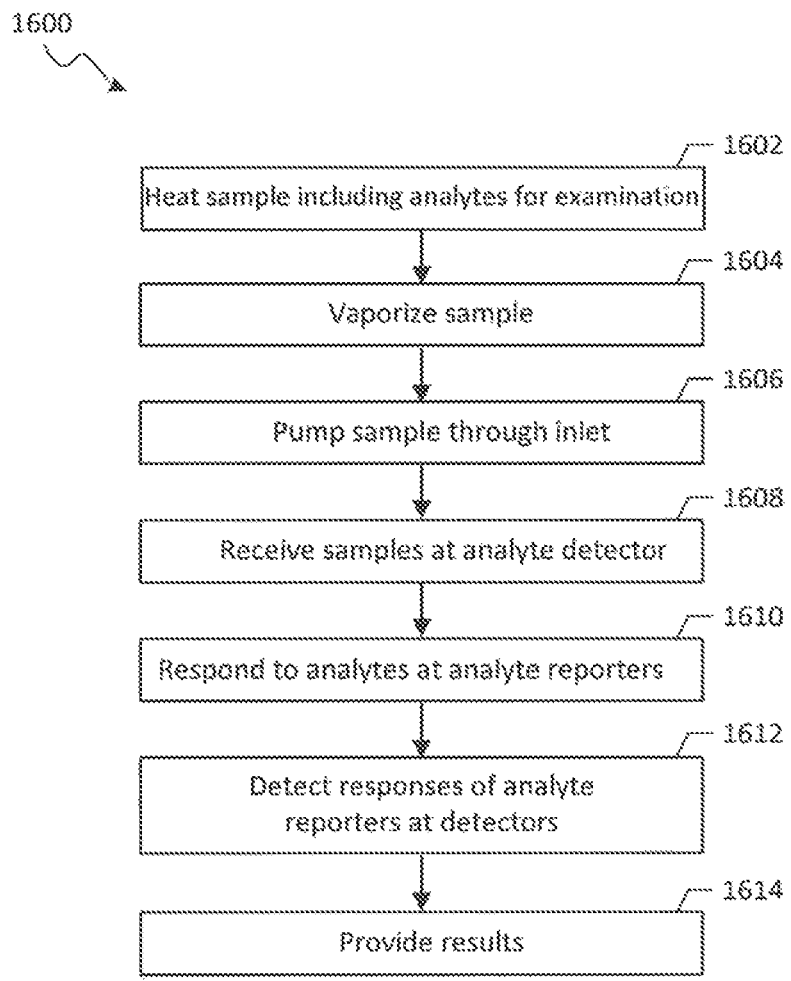
FIG. 16 illustrates a process of operating a system to perform chemical detection of a sample for examination in accordance with an embodiment of the disclosure.

FIG. 16 illustrates a process 1600 of operating the system 100 to perform chemical detection of a sample for examination in accordance with an embodiment of the present disclosure. In an embodiment, the process 1600 may be performed during blocks 1506 and/or 1516 of FIG. 15. Such process detail may apply to techniques that use emission (e.g., fluorescent and luminescent) techniques.

At block 1602, the heater 336 applies heat to sample for examination. For example, the sample may be the test samples (e.g., 406A-C) provided on sampling media (e.g., 402) during normal operation or a selected calibrant during a calibration operation. In various embodiments, the heater 336 may be operated in response to the user's operation of one or more user controls 106 and/or automatically in response to disposing of the sample into the chamber 334, e.g. the insertion of the sampling media 402 into the chamber 334 or the rotating of the calibrant reservoir into the chamber 334. In some cases, the heater 316A may also be operated to apply heat to the sample.

At block 1604, the sample is at least partially vaporized to provide analytes (e.g., 404) in response to the heat applied by the heater 336. In some cases, the heater 336 is moved in contact with the sample. At block 1606, the pump 314 is operated to draw at least a portion of the sample including the analytes through the inlet 202 and out through the outlet 312. At block 1608, the analytes are received by the analyte detector 318.

In some embodiments, alternative and/or in addition heating the sample, one or more fans and/or pumps may push or pull at least a portion of the sample, which may include analytes, to provide the portion of the sample to the analyte detector 318 via the inlet 202. In such embodiments, the analytes may be, but need not be, vaporized analytes. In some cases, the fan(s) and/or pump(s) may be included in the calibration device 104 alternatively and/or in addition to the pump 314 of the detection device 102.

At block 1610, one or more of the analyte reporters 320A-C of the analyte detector 318 respond to the analytes. In some cases, the analytes are exposed to the analyte reporters 320A-C by being passed through (e.g., drawn through by the pump 314) the analyte reporters 320A-C. For example, different analyte reporters may respond to different portions (e.g., components) of the analytes. For example, the analyte reporter 320A may respond to certain military explosives and/or explosive-related compounds present in the analytes while the analyte reporter 320B may respond to certain amine-based substances in the analytes. In some cases, the illuminators 322A and 322B may be used to facilitate a response from the analytes once the analytes have been exposed to the analyte reporters 320A and 320B, respectively.

At block 1612, the response detectors 324A-C detect responses of the analyte reporters 320A-C to the analytes. For example, during normal operation, the response detector 324A detects the response of the analyte reporter 320A to the portion of the analytes corresponding to the test sample 406A, response detector 324B detects the response of the analyte reporter 320B to the portion of the analytes corresponding to the test sample 406B, and response detector 324C detects the response of the analyte reporter 320C to the portion of the analytes corresponding to the test sample 406C. As another example, during a calibration operation, the response detectors 324A-C detect the response of the analyte reporters 320A-C to the analytes (e.g., the vaporized calibrants) that are passed through the analyte reporters 320A-C.

At block 1614, results are provided. In some cases, the results may be provided to and/or derived by the processor 302 (e.g., based on detected responses). Depending on operation of the system 100, the results may be for a detection process (e.g., normal operation) or a test process (e.g., calibration operation). For example, during normal operation, the results may be whether a material of interest is determined to be present in the test samples. During a calibration operation, the results may indicate whether the analyte reporters 320A-C are operating properly. The response data from the response detectors 324A-C may also be provided. In some cases, the results may be provided to the user (e.g., via the display 108).

In view of the present disclosure, it will be appreciated that various embodiments provided herein can be used for facilitating chemical detection of materials of interest and calibration of associated chemical detection systems. In particular, an attachment as provided herein may be used to selectively perform in field detection operations and in field calibration operations in a low cost, rapid, and highly portable manner with minimal or no user interaction. Notably, an actuated calibrant wheel with one or more associated calibrant reservoirs may be efficiently used to selectively position the calibrant reservoirs in a chamber that is also used to receive test samples. As a result, both in field testing and in field calibration can be efficiently performed. Moreover, chemical detection systems implemented in the manner disclosed herein may avoid errors and/or inconvenience associated with conventional manual calibration, operations.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A system comprising:
a calibration device configured to operate with an analyte detector, the calibration device comprising:
a chamber configured to receive a sample and pass at least a portion of the sample comprising analytes to the analyte detector for examination;
a reservoir comprising a calibrant and configured to be selectively positioned in the chamber as the sample to provide the portion of the sample comprising the analytes to calibrate the analyte detector;
a wheel comprising the reservoir; and
an actuator configured to rotate the wheel to position the reservoir in the chamber.

2. The system of claim 1, further comprising a sample extraction component configured to propel the portion of the sample from the chamber to the analyte detector, wherein the sample extraction component is at least one of:
a heater configured to at least partially vaporize the sample to provide the portion of the sample; and/or
a pump.

3. The system of claim 1, further comprising the analyte detector and a processor configured to detect a response of the analyte detector to the analytes and perform an action based on the detected response.

4. The system of claim 3, wherein the action is a notification to replace the calibrant and/or an adjustment of a setting of the analyte detector.

5. The system of claim 1, wherein:
the reservoir is a first reservoir and the calibrant is a first calibrant;
the wheel further comprises a second reservoir comprising a second calibrant; and
the first and second calibrants are each associated with one or more analyte reporters of the analyte detector.

6. The system of claim 1, wherein the wheel further comprises a sealing member configured to be positioned in the chamber and against an inlet associated with the analyte detector, and wherein the system further comprises a processor configured to detect leaks associated with the analyte detector while the sealing member is positioned against the inlet.

7. The system of claim 1, wherein the calibration device further comprises:
a blocking member configured to prevent insertion of external media as the sample when the reservoir is in position in the chamber; and
a chamber detector configured to prevent rotation of the wheel when the external media is in position in the chamber as the sample.

8. The system of claim 1, wherein the calibration device further comprises a barrier configured to prevent transfer of the portion of the sample between the chamber and the reservoir while the reservoir is not positioned in the chamber.

9. The system of claim 1, wherein the reservoir comprises:
a base, side walls, and a lid defining a volume configured to store the calibrant;
a vent in the lid configured to pass the portion of the sample to the analyte detector; and
wherein the reservoir further comprises at least one of:
a plurality of protrusions in the base configured to increase an interior surface area of the reservoir to receive the calibrant; and/or
a mesh configured to maintain the calibrant in solid form within the volume and pass the calibrant in vaporized form to the vent to provide the portion of the sample.

10. The system of claim 1, wherein the calibration device is a modular accessory configured to be selectively attached to a housing associated with the analyte detector.

11. A method comprising:
initiating a calibration operation to calibrate an analyte detector;
positioning a reservoir in a chamber of a calibration device in response to the initiating, wherein the reservoir comprises a calibrant;
providing at least a portion of the calibrant comprising analytes to the analyte detector;
detecting a response of the analyte detector to the analytes;
determining whether the analyte detector is operating properly based at least on the detected response;
wherein the calibration device further comprises a wheel comprising the reservoir, and an actuator; and
wherein the positioning comprises rotating, using the actuator, the wheel to position the reservoir in the chamber.

12. The method of claim 11, wherein the providing the portion of the calibrant comprises operating a sample extraction component to propel the portion of the calibrant from the chamber to the analyte detector, wherein the sample extraction component is at least one of:
a heater configured to at least partially vaporize the calibrant to provide the portion of the calibrant; and/or
a pump.

13. The method of claim 11, further comprising performing at least one action based on the determining, wherein the at least one action is a notification to replace the calibrant and/or an adjustment of a setting of the analyte detector.

14. The method of claim 11, wherein:
the reservoir is a first reservoir and the calibrant is a first calibrant;

the wheel further comprises a second reservoir comprising a second calibrant; and the first and second calibrants are each associated with one or more analyte reporters of the analyte detector.

15. The method of claim 11, wherein the wheel further comprises a sealing member, the method further comprising:

positioning the sealing member in the chamber and against an inlet associated with the analyte detector; and detecting at least one leak associated with the analyte detector while the sealing member is positioned against the inlet.

16. The method of claim 11, further comprising:

preventing, using a blocking member of the calibration device, insertion of external media when the reservoir is in position in the chamber; and preventing, using a chamber detector of the calibration device, rotation of the wheel when the external media is in position in the chamber.

17. The method of claim 11, further comprising:

preventing, using a barrier of the calibration device, transfer of material between the chamber and the reservoir while the reservoir is not positioned in the chamber.

18. The method of claim 11, wherein the reservoir comprises:

a base, side walls, and a lid defining a volume configured to store the calibrant;

a vent in the lid configured to pass the portion of the calibrant to the analyte detector;

wherein the reservoir further comprises at least one of:

a plurality of protrusions in the base configured to increase an interior surface area of the reservoir to receive the calibrant; and/or a mesh configured to maintain the calibrant in solid form within the volume and pass the calibrant in vaporized form to the vent to provide the analytes; and wherein the calibration device is a modular accessory configured to be selectively attached to a housing associated with the analyte detector.

* * * * *

UNITED STATES PATENT AND TRADEMARK OFFICE
CERTIFICATE OF CORRECTION

PATENT NO. : 11,360,065 B2
APPLICATION NO. : 16/352661
DATED : June 14, 2022
INVENTOR(S) : John B. Lynch, Martin Sanders and Chris Willis It is certified that error appears in the above-identified patent and that said Letters Patent is hereby corrected as shown below:

In the Specification

In the Detailed Description:

In Column 21, Line 21, change "reporter 3200" to --reporter 320C.--.

In Column 25, Line 9, change "reporter 3208" to --reporter 320B--.

In Column 25, Line 28, change "reporter 3200" to --reporter 320C--.

Signed and Sealed this
Sixth Day of September, 2022

Katherine Kelly Vidal
*Director of the United States Patent and Trademark Office*